(12) United States Patent
Tandon

(10) Patent No.: US 7,162,929 B2
(45) Date of Patent: Jan. 16, 2007

(54) SYSTEM AND METHOD FOR FIELD TESTING A TACK COAT LAYER

(75) Inventor: Vivek Tandon, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 5 days.

(21) Appl. No.: 10/937,102

(22) Filed: Sep. 9, 2004

(65) Prior Publication Data

US 2005/0238428 A1    Oct. 27, 2005

Related U.S. Application Data

(60) Provisional application No. 60/565,767, filed on Apr. 27, 2004.

(51) Int. Cl.
G01N 3/08    (2006.01)

(52) U.S. Cl. .......................................... 73/827; 404/75

(58) Field of Classification Search .................. 404/75; 73/150 R, 150 A, 827, 862.21, 862.22
See application file for complete search history.

(56) References Cited

U.S. PATENT DOCUMENTS 6,846,039 B1 *    1/2005    Lewno ....................... 296/201

OTHER PUBLICATIONS

Caduto, *Geotechnical Engineering Principles and Practices*, Prentice Hall, 500-503, 1998.

Deysarkar and Tandon, "Field evaluation of tack coat quality measurement equipment," Accepted for publication in: *International Journal of Pavement*, 2005.

Hachiya and Sato, "Effect of tack coat on bonding characteristics at interface between asphalt concrete layrers," *Eighth International Conference on Asphalt Pavements Proceedings*, 1:349-362, 1997.

Mohammad et al., "Influence of asphalt tack coat materials on interface shear strength," *Transportation Research Record 1789*, Transportation Research Board, Washington, DC, 56-65, 2002.

Ronanoschi and Metcalf, "Characterization of asphalt concrete layer interfaces," *Transportation Research Record 1778*, Transportation Research Board, Washington, DC, 132-138, 2001.

Santagata et al., "Laboratory shear testing of tack coat emulsions," $1^{st}$ *World Congress on Emulsion*, Paris, 10-118/1-6, 1993.

Sholar et al., "Preliminary investigation of a test method to evaluate bond strength of bituminous tack coats," *Journal of Asphalt Paving Technologists*, 73:771-801, 2004.

(Continued)

*Primary Examiner*—Edward Lefkowitz
*Assistant Examiner*—Lori Moorman
(74) *Attorney, Agent, or Firm*—Fulbright & Jaworski LLP

(57) ABSTRACT

Methods and systems are disclosed for evaluating an adhesive layer such as a tack coat. In one embodiment, a portable apparatus is provided to test a tack coat layer prior to applying an overlay. The portable apparatus includes a tripod configuration placed on a surface, a plate conformed to the surface by a load and a torque wrench-applying a pull-off force to test the strength of the surface. In other embodiments, a portable apparatus is provided to test a tack coat layer prior to applying an overlay, where the portable apparatus does not include support members.

27 Claims, 12 Drawing Sheets

OTHER PUBLICATIONS

Uzan et al., "Investigation of adhesion properties between asphaltic-concrete layers," *Journal of Asphalt Paving Technologists*, 47:495-521, 1978.

Youtcheff and Aurilio, "Moisture sensitivity of asphalt binders: evaluation and modeling of the pneumatic adhesion test results," *Proceedings of the Annual Conference-Canadian Technical Asphalt Association 0068-984X*, 42:180-200, 1997.

Nazarian et al., "Specifications for tools used in structural field testing of flexible pavement layers," *Research Report 1735-1, The Center for Highway Materials Research, The University of Texas at El Paso*, Aug. 1998.

Buchanan and Woods, "Field Tack Coat Evaluator (ATACKer™) Report No. FHWA/MS-DOT-RD-04-168," *Mississippi State University, Department of Civil Engineering, Construction Materials Research Center*, Dec. 15, 2004.

Letter to Dr. Barry A. Benedict from President of InstroTek Inc., 2 pages, Apr. 12, 2006.

* cited by examiner

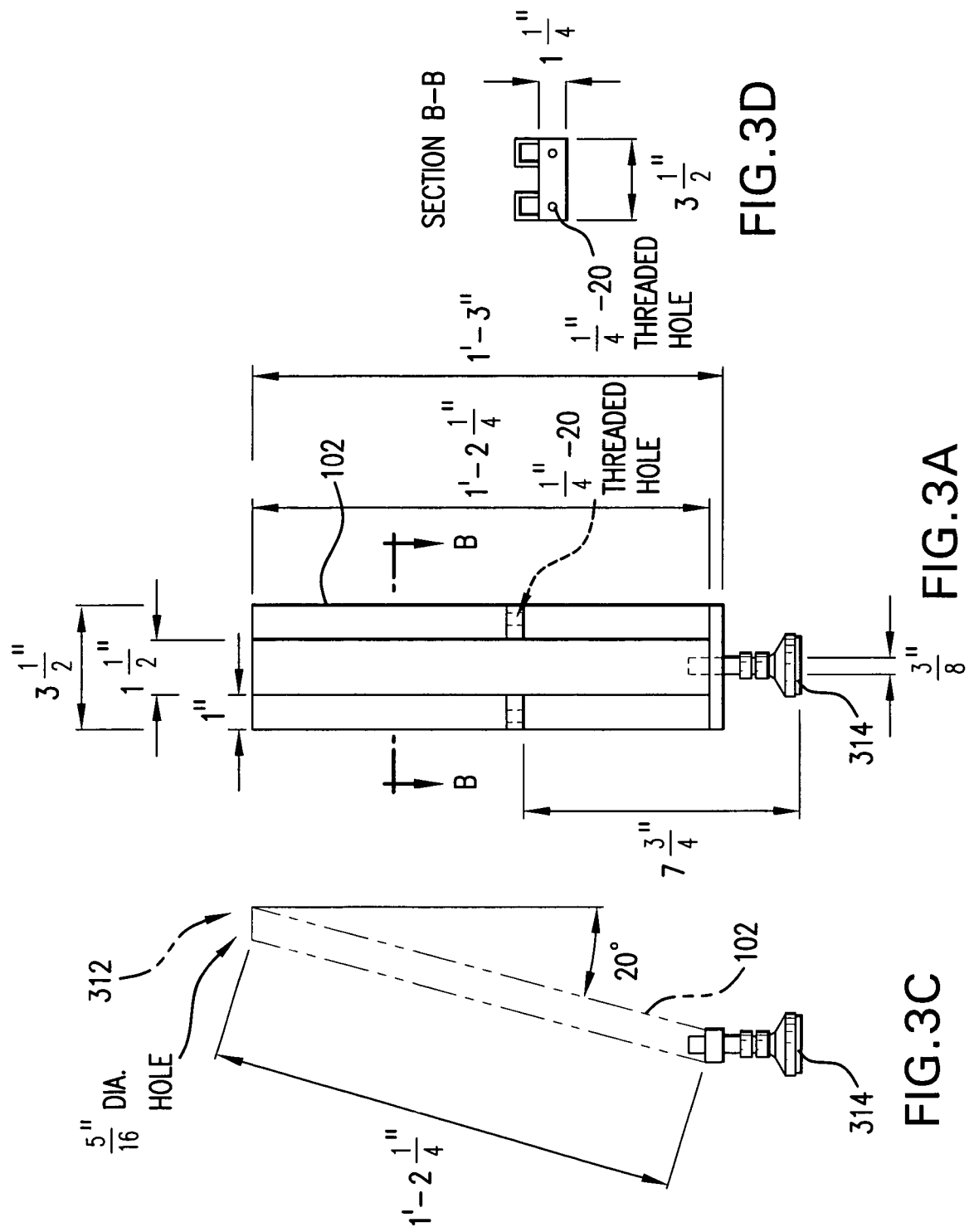

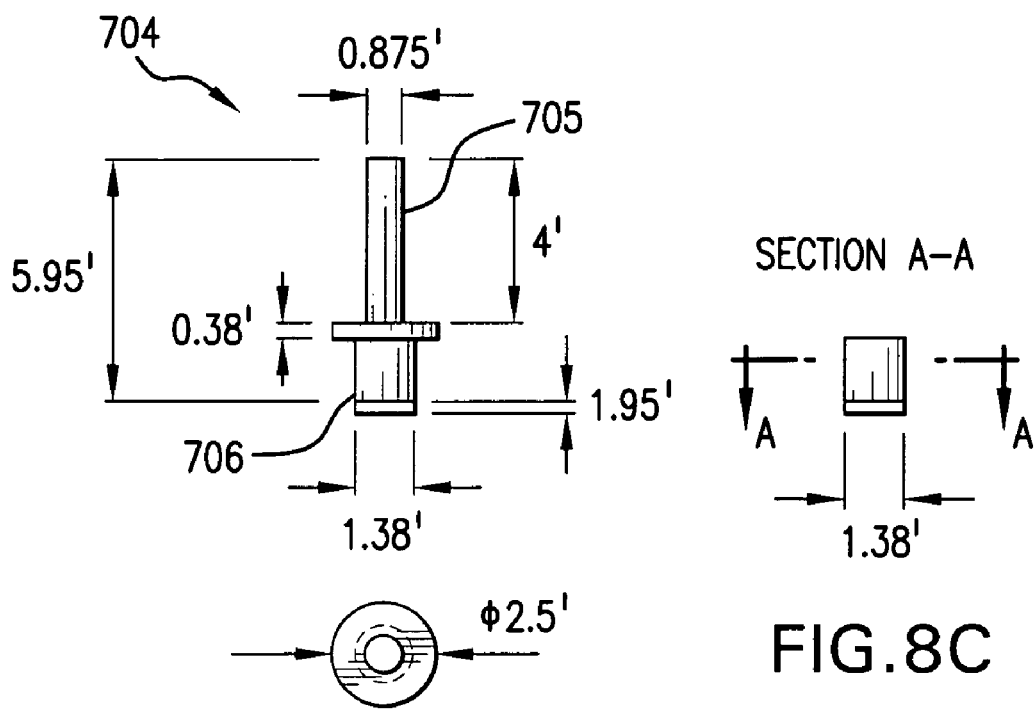
FIG.8A
SECTION A-A
FIG.8C
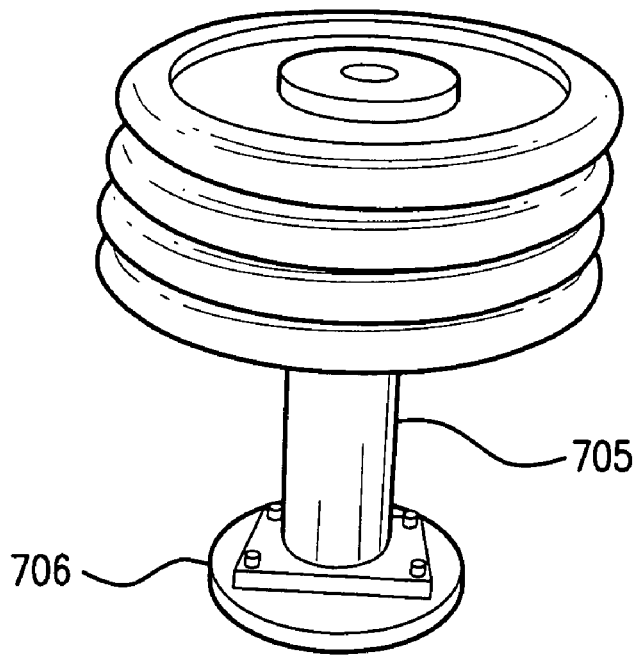
FIG.8B

SYSTEM AND METHOD FOR FIELD TESTING A TACK COAT LAYER

This patent application claims priority to, and incorporates by reference in its entirety, U.S. provisional patent application Ser. No. 60/565,767 filed on Apr. 27, 2004.

Aspects of this invention were made with government support by Texas Department of Transportation Contract/Grant No. 0-4129. The government may accordingly have certain rights in this invention.

BACKGROUND OF THE INVENTION

I. Field of the Invention

The present invention relates to testing adhesion layers. More particularly, this invention describes methods and systems for testing the quality of tack coat layers applied on road surfaces before placement of an overlay to provide for bonding.

II. Description of Related Art

The U.S. Department of Transportation Federal Highway Administration estimates that about 50% of the interstate system and about 70% of all highways in the U.S. are paved with hot-mix asphalt concrete (HMAC). However, there is evidence that the number of premature distresses to the constructed asphalt pavement is increasing. Factors such as heavier truck axle weights, increased tire pressures, increased traffic loading, and/or inadequate drainage contribute to the deterioration of the pavement system.

Typically, to strengthen the deteriorated pavement system, an overlay of HMAC (approximately 2 in thick) is placed on top of the existing pavement. This tack coat, comprising materials such as emulsions or asphalt cements, is generally applied to existing surfaces prior to applying an overlay. The tack coat acts as a thin layer that bonds overlay to the existing surface. In cases where bond loss occurs between the existing surface and the overlay, a slippage occurs between the layers, causing failure. The loss of bondage can be attributed to at least the following: quality of the tack coat, application of the tack coat, dilution of the tack coat, and materials settling on the tack coat (e.g., dust, rainfall, etc.) prior to applying the overlay As such, it is necessary to be able to test the strength of the tack coat prior to the application of the overlay. Current methods observe and analyze samples in laboratories to determine the best tack coat type and rate of application of the tack coat. However, laboratory observation does not factor in environmental constraints that may alter the composition and effectiveness of the tack coat. Further, laboratory evaluations do not allow for on-site evaluation of the tack coat to insure the quality of the tack coat prior to applying the overlay.

The referenced shortcomings are not intended to be exhaustive, but rather are among many that tend to impair the effectiveness of previously known techniques concerning testing of a tack coat; however, those mentioned here are sufficient to demonstrate that the methodologies appearing in the art have not been altogether satisfactory and that a significant need exists for the techniques described and claimed in this disclosure.

SUMMARY OF THE INVENTION

Thus, there is a need for methods and systems that provide an efficient and accurate field-testing of tack coats after the tack coat is applied and prior to the application of an overlay.

In one embodiment, the invention involves an apparatus. The apparatus may include a plurality of supporting members, a contact plate coupled to the plurality of supporting members, in which the contact plate may adhere to the shape of a pavement surface. The apparatus may also include a torque wrench and force measuring device which applies a force onto the pavement surface and determines the strength of the pavement surface.

In another embodiment, an apparatus includes supporting members and an elevation member disposed between the supporting member. The elevation member moves a contact plate of the apparatus into direct contact with a pavement surface. A torque wrench coupled to the supporting members applies a pull-off force for testing the adhesive quality of the tack coat layer.

In yet another embodiment, an apparatus includes a contact plate that adheres and conforms to a pavement surface. The apparatus also includes a torque wrench and a force measuring device coupled to the contact plate for pulling up the contact plate and measuring the strength of the pavement surface.

In another respect, the invention involves a method. A tripod may be provided and may include a plate, support members, an elevation member, and a torque wrench. The support members support the plate substantially parallel to the surface. The elevation member may move the plate into direct contact with a surface. A load, applied to the plate, may conform the plate to the surface. The torque wrench may apply a force onto the surface and may test the strength of the surface.

According to another embodiment, the invention involves a method. An apparatus with a contact plate, an elevation member coupled to the contact plate for placing the contact plate in direct contact with a pavement surface, and a torque wrench coupled to the contact plate for testing the strength of the pavement is provided. A load is applied to the elevation member to conform the contact plate to the pavement surface. By rotating the torque wrench about an axis, the strength of the pavement surface may be determined.

The use of the word "a" or "an" when used in conjunction with the term "comprising" in the claims and/or the specification may mean "one," but it is also consistent with the meaning of "one or more," "at least one," and "one or more than one." The term coupled, as used herein, is defined as connected, although not necessarily directly, and not necessarily mechanically.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A–3D illustrate details of supporting members of an apparatus in accordance with embodiments of the disclosure.

FIGS. 8A–8C illustrate details of a weight key of an apparatus in accordance with embodiments of the disclosure.

DESCRIPTION OF ILLUSTRATIVE EMBODIMENTS

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

General embodiments of the present invention provide apparatuses and methods for on-site testing of a pavement surface, such as a bonding layer prior to applying an overlay. In one embodiment, the apparatuses and methods identify the adhesive quality of the tack coat. For example, the apparatuses and methods may test the strength of the tack coat to determine if the tack coat will properly bond the existing layer and the overlay. As such, the present invention can reduce or even eliminate distresses to surfaces caused by bond loss.

Figure 1:
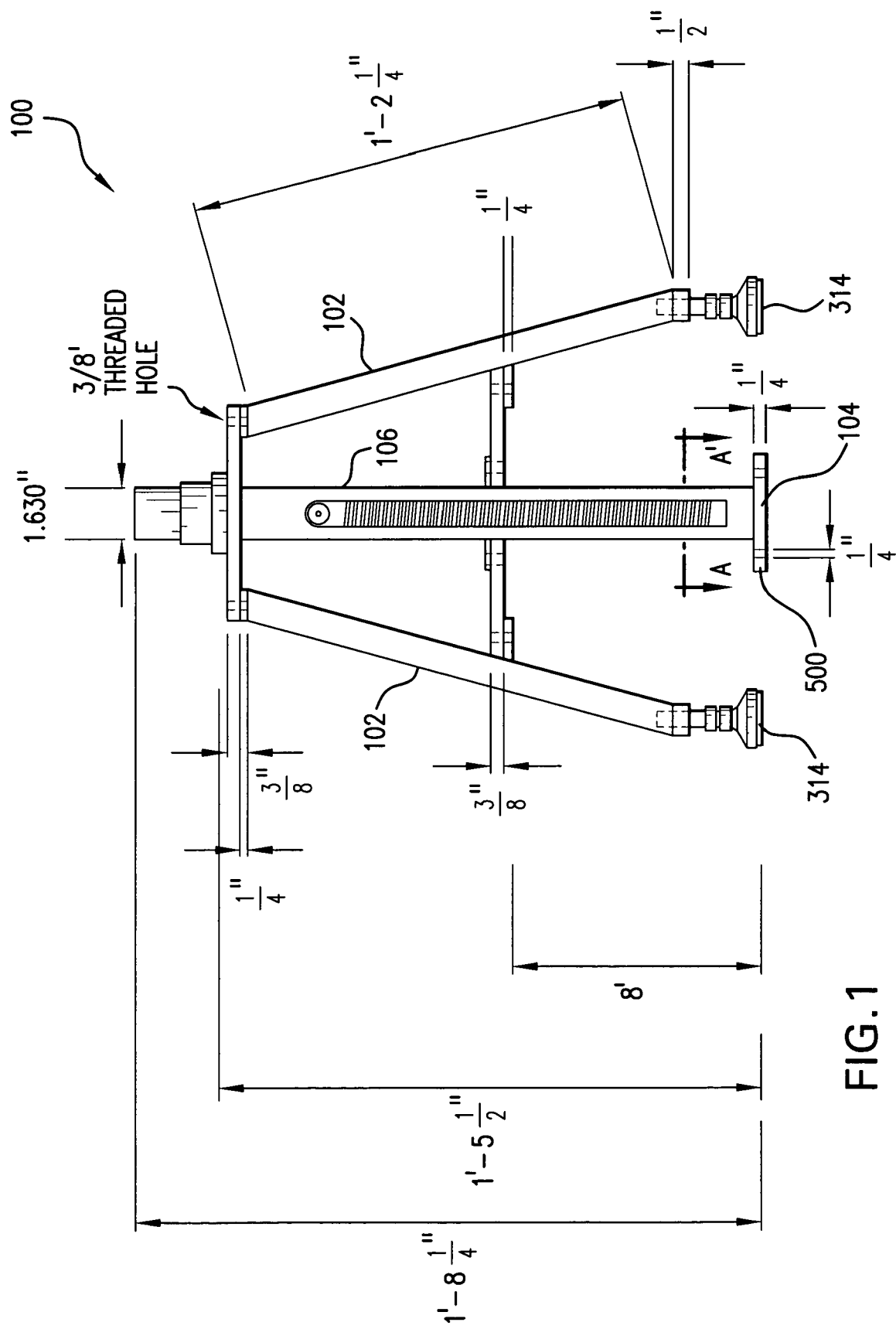
FIG. 1 illustrates an apparatus in accordance with embodiments of the disclosure.
Figure 2:
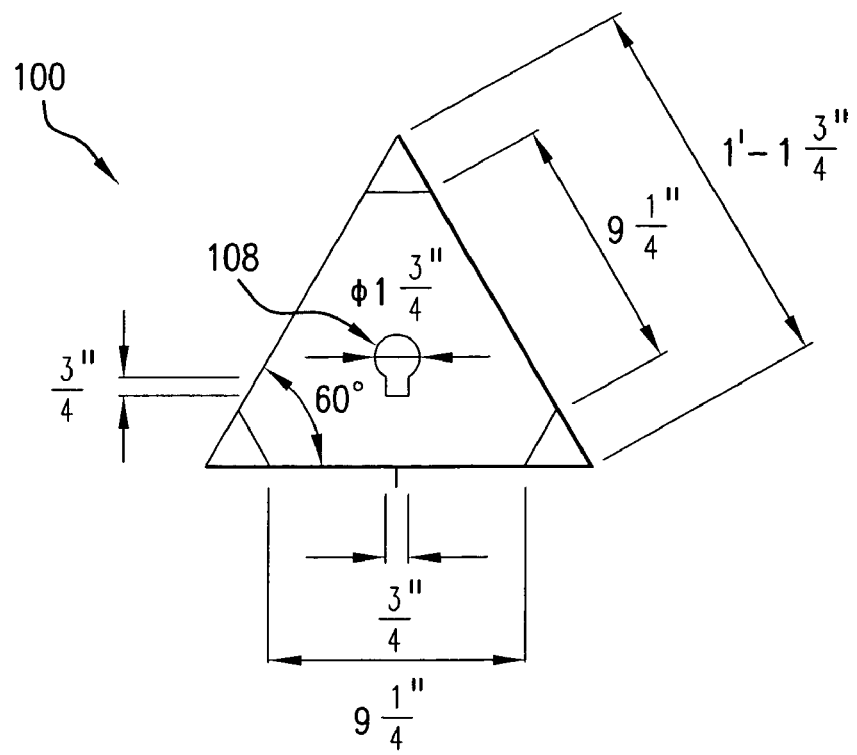
FIG. 2 illustrates a top-plate of an apparatus in accordance with embodiments of the disclosure.
Figure 3B:
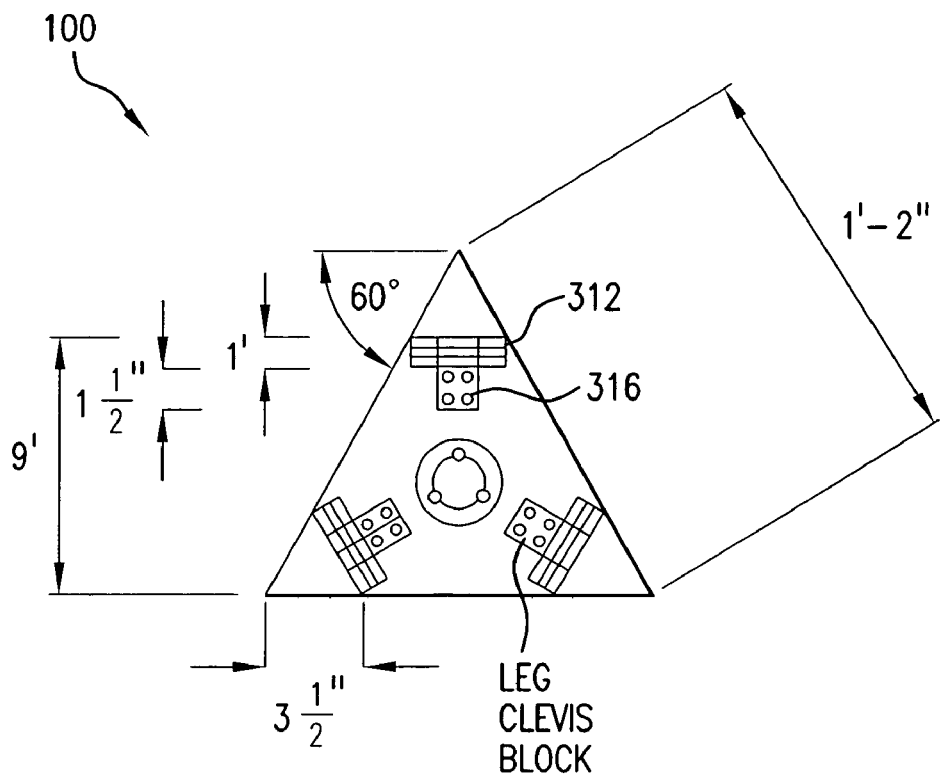

A diagram of an apparatus that can be used to test a pavement surface is illustrated in FIG. 1. Apparatus 100 may include support members 102. In one embodiment, the support members 102 may include three legs positioned in a tripod configuration, as illustrated in a top-view diagram of the apparatus 100 in FIG. 2. The configuration provides stability when the tripod is placed on the pavement surface. In particular, the support members 102 may provide stability due to pivoting feet 314 (e.g., FIG. 3A and FIG. 3C) attached to each support member. The pivoting feet 314 may allow the apparatus to self-level upon placement on a surface, such that the contact plate 104 is substantially parallel to the pavement surface. Additionally, the support members 102 may be adjustable to different heights and may also be flexible to move within a horizontal plane to further stabilize the apparatus. Referring to FIG. 3C, each support member of the apparatus 100 may be operably moveable in a horizontal plane within a 0° to 20° range. In other embodiments, different ranges of angles can be achieved. A clevis block 312 may be provided to allow the pivotal motion of the support member, in which clevis block 312 may include hinge 316, as illustrated in the top-view diagram of the apparatus 100 in FIG. 3B.

Figure 4:
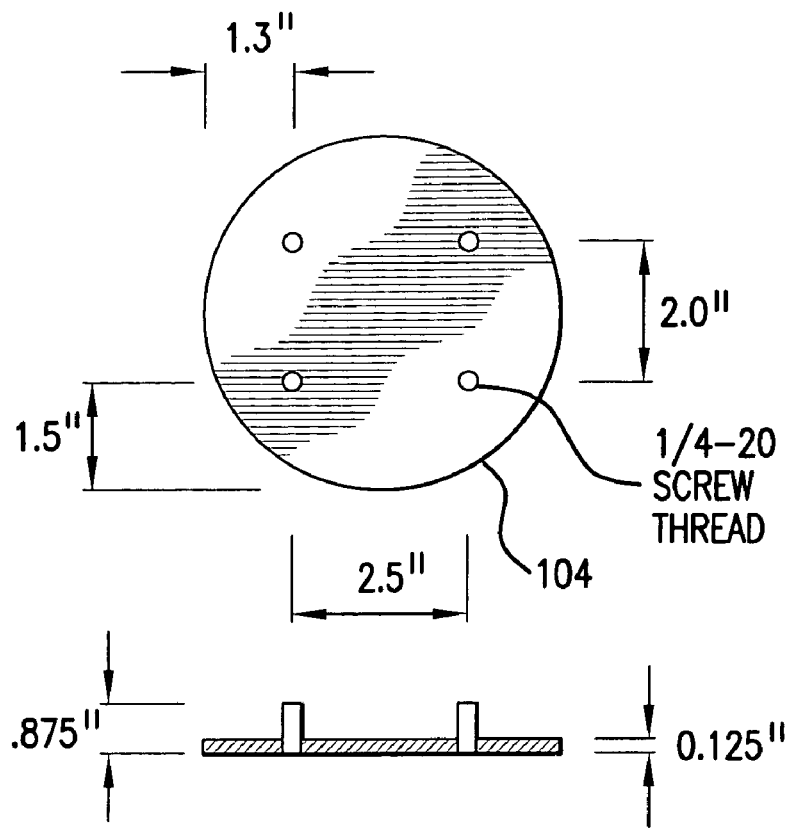
FIG. 4 illustrates a contact plate of an apparatus in accordance with embodiments of the disclosure.

The apparatus 100 may also include a contact plate 104, disposed between the support members 102 as shown in FIG. 1. In one embodiment, contact plate 104 may be a circular plate, as illustrated in FIG. 4. Alternatively, contact plate 104 may be of any shape or dimension. The contact plate 104 may be situated and supported by the support members 102 in a manner substantially parallel relative to a pavement surface. When a load is applied to the apparatus, the contact plate may directly contact the surface, stabilizing the apparatus. In embodiments where the surface is not smooth, the contact plate 104 may have a thickness that would allow the contact plate to conform to the shape of the tack coat layer, to further steady and balance the apparatus. In one embodiment, the thickness of the plate may be 0.125 inches but can range up to 0.75 inches. It will be understood that other dimensions can be used.

The contact plate 104 may also include a flexible layer for properly adhering the contact plate 104 to the tack coat surface before testing. In one embodiment, the flexible layer includes a flexible adhesive layer where the flexible adhesive layer may include, but is not limited to tape, double-sided tape, double-sided tape with a protective adhesive covering, epoxy layers, or any other adhesive component that may allow contact plate 104 to adhere to the pavement surface. The contact plate 104 may also include a flexible shape conforming layer that may include, but is not limited to, moisture bearing foam to better conform to the pavement surface. In one embodiment, the moisture bearing foam may be attached to the flexible adhesive layer. The foam may compress when a load is applied to apparatus 100 to insure a proper adhesion of the contact plate to the tack coat layer.

Figure 5:
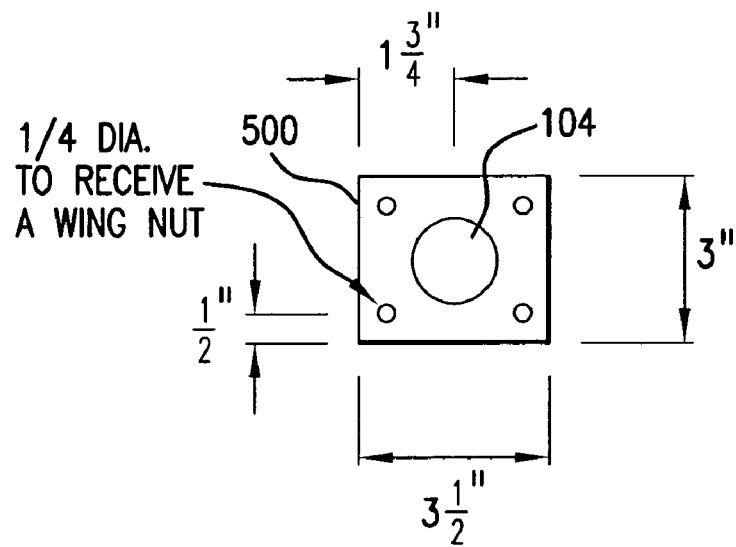
FIG. 5 illustrates a footing (coupled to a contact plate) of an elevation member in accordance with embodiments of the disclosure.

Apparatus 100 may also include an elevation member 106 which may move contact plate 104 in a vertical manner into direct contact with the surface. The elevation member 106 may be disposed between support members 102 through a key hole 108 of apparatus 100, as illustrated in FIG. 2. The elevation member 106 may include a footing 500 as depicted between A and A' as shown in FIG. 1 and further detailed in FIG. 5. The footing 108, with contact plate 104 disposed within, may ground the elevation member 106 to the surface and may also provide stability to the apparatus during testing.

In one embodiment, the elevation member 106 includes a manual-controlled cylinder operably moveable in a vertical direction to place the contact plate 104 in direct contact with the pavement surface. In yet another embodiment, elevation member 106 includes a pneumatic-controlled cylinder which may lower the contact plate 104 in direct contact with a pavement surface. The vacuum or air-pressure may be measured by a sensor to determine the adhesive quality of the pavement surface. Alternatively, the cylinder may be a hydraulic-controlled cylinder, a spring-loaded cylinder, or a motor-controlled cylinder, each operable moveable in a vertical manner to place the contact plate 104 into direct contact with a tack coat layer.

Figure 6:
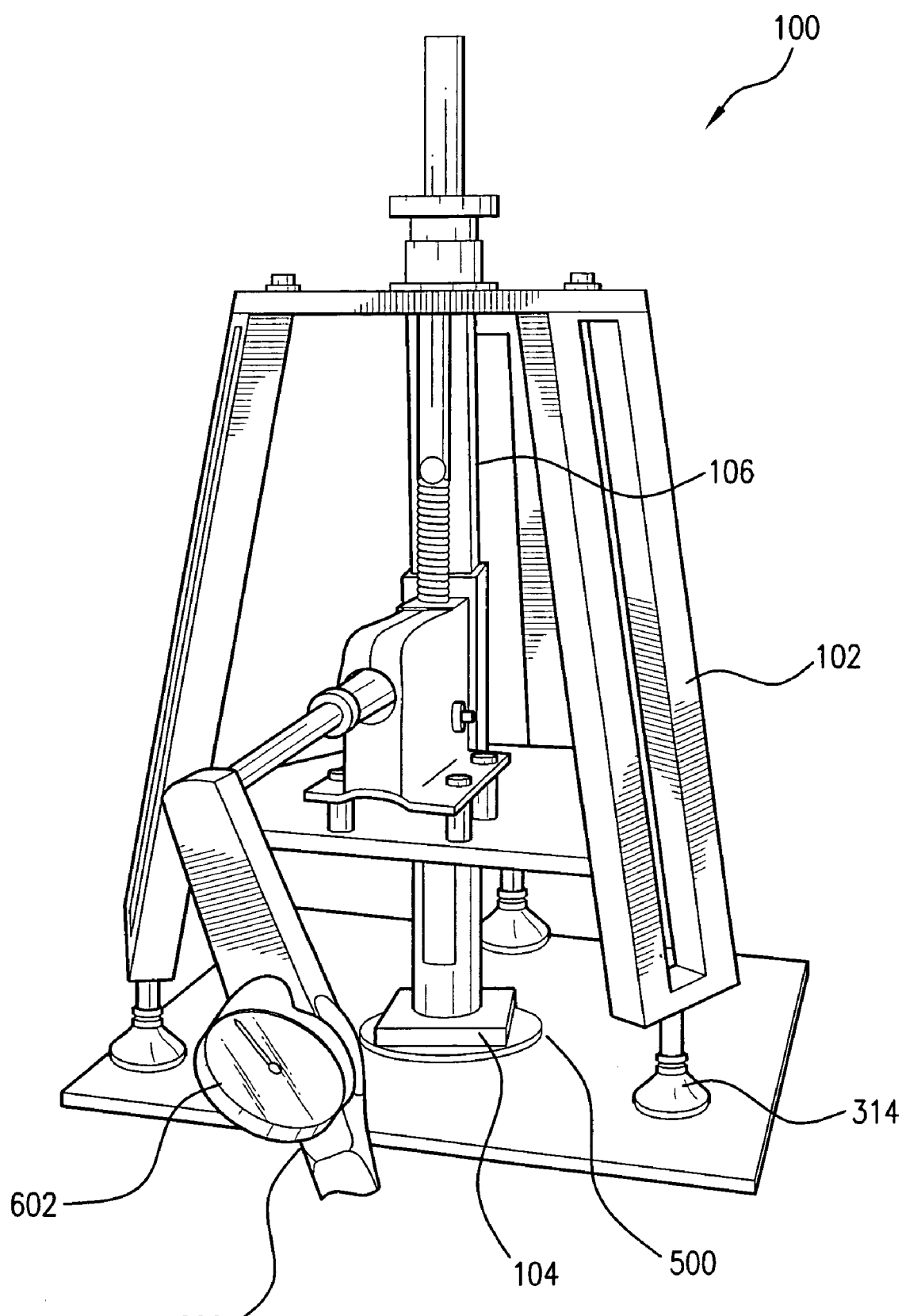
FIG. 6 illustrates an apparatus in accordance with embodiments of the disclosure.

A torque wrench may also be provided. Referring to FIG. 6, apparatus 100 includes a torque wrench 600 coupled to the elevation member 106. Upon placing and stabilizing the apparatus 100 upon the pavement surface, the torque wrench may be used to pull-up a portion of the tack coat layer to determine the adhesive quality of the tack coat. In one embodiment, torque wrench 600 may be able to determine the strength of the tack coat by the force, such as a torque force, needed to rotate the torque wrench about a horizontal axis parallel to the surface. A force measuring device 602 coupled to the torque wrench 600 may record the breaking torque. As such, if the strength of the tack coat is determined to be of poor quality, adjustments can be made to the tack coat layer prior to applying the overlay.

Figure 7:
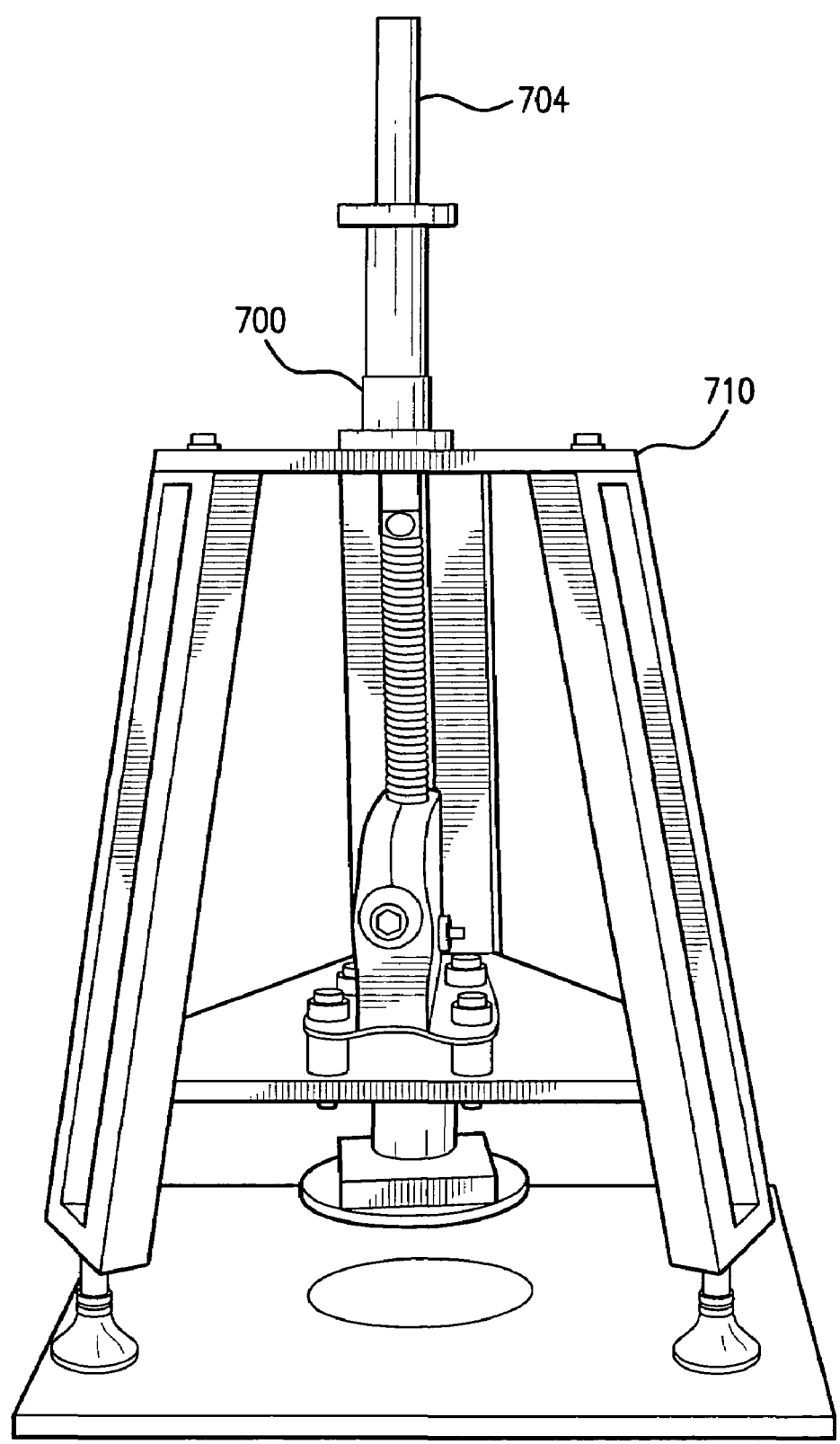
FIG. 7 illustrates an apparatus in accordance with embodiments of the disclosure.
Figure 7A:
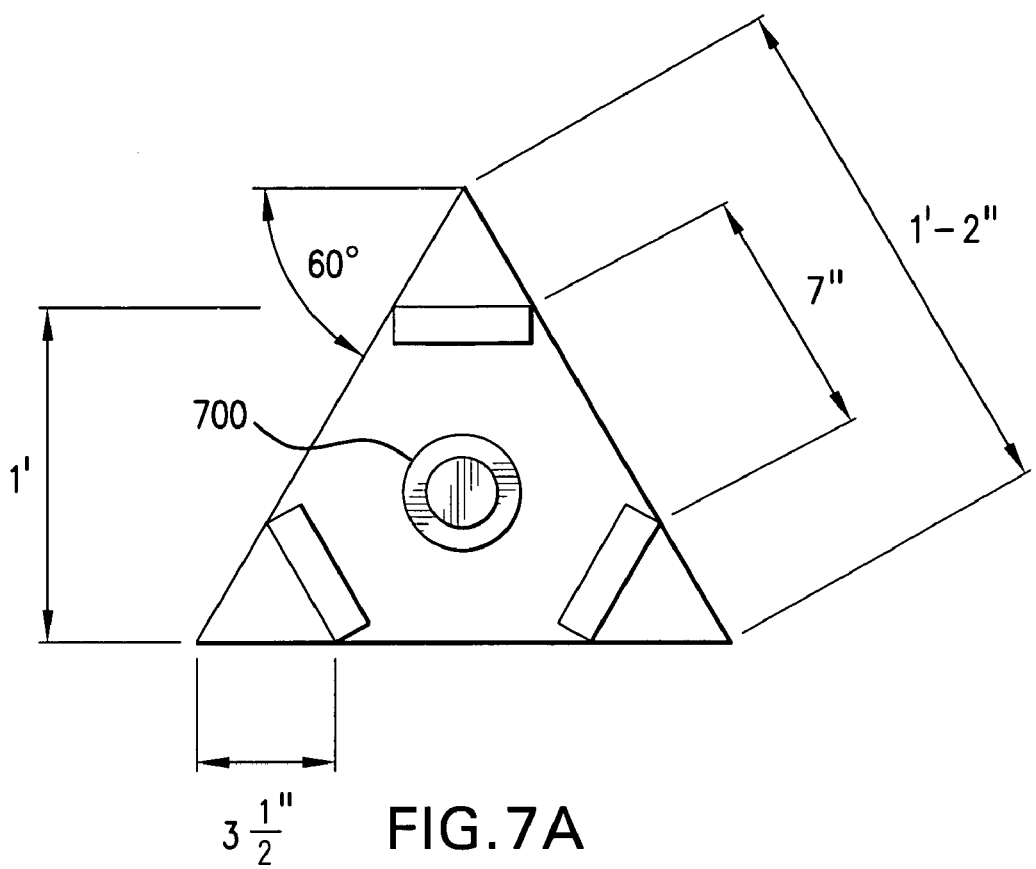
FIGS. 7A–7C illustrate details of a shaft sleeve of an apparatus in accordance with embodiments of the disclosure.
Figure 7B:
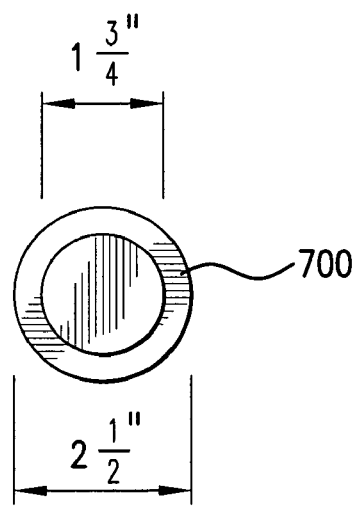
Figure 7C:
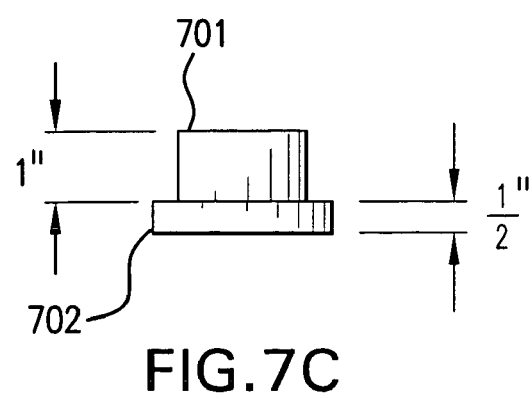

The apparatus 100 may also include a shaft sleeve 700 placed on top of top plate 710, as shown in FIG. 7. The shaft sleeve 700 may be used to reduce friction when the elevation member 106 moves in a vertical manner. The shaft sleeve may be a Teflon shaft sleeve or made of an ultra high molecular weight material or ball bearing type or friction reducing component. In one embodiment, the shaft sleeve may include a first portion 701 and a second portion 702 as illustrated in FIG. 7B and FIG. 7C. The second portion 702 surrounds the key hole 108 in which elevation member 106 may be displaced, as seen in FIG. 7A.

Further, the apparatus 100 may also include a weight key 704, as shown in FIG. 7. The weight key may be coupled to the elevation member 106 and may receive a load. In one embodiment, a load can be applied on the first portion 705 to receive the load and a second portion 706 to hold the load in place, as illustrated in FIGS. 8A, 8B, and 8C. The load may apply a pressure onto the contact plate 104 to aid the adhesion of the contact plate to the pavement surface.

Figure 9:
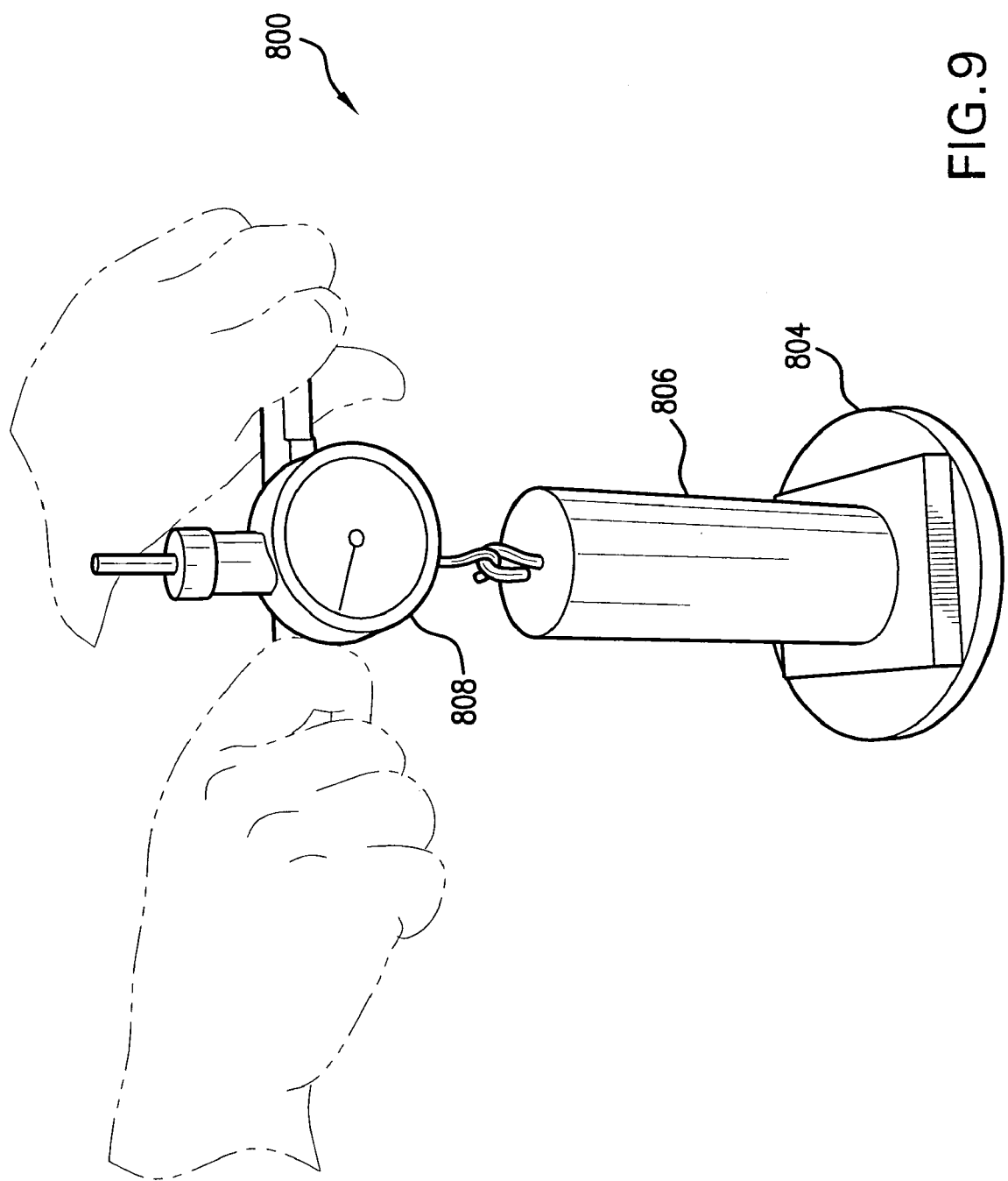
FIG. 9 illustrates an apparatus in accordance with embodiments of the disclosure.
Figure 10A:
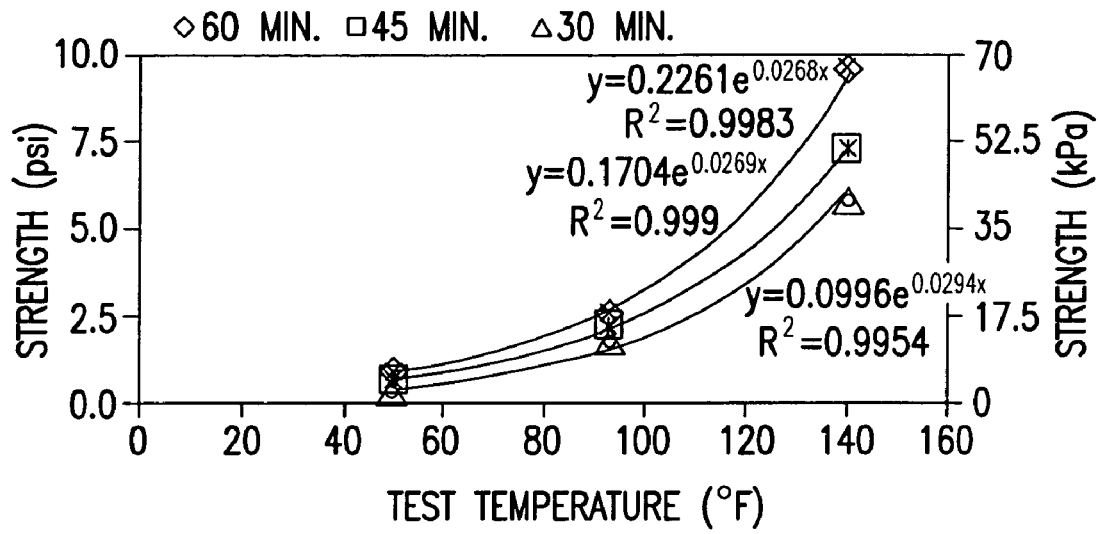
FIGS. 10A–10E illustrate test results of various tack coat types with varying temperatures and set rate.
Figure 10B:
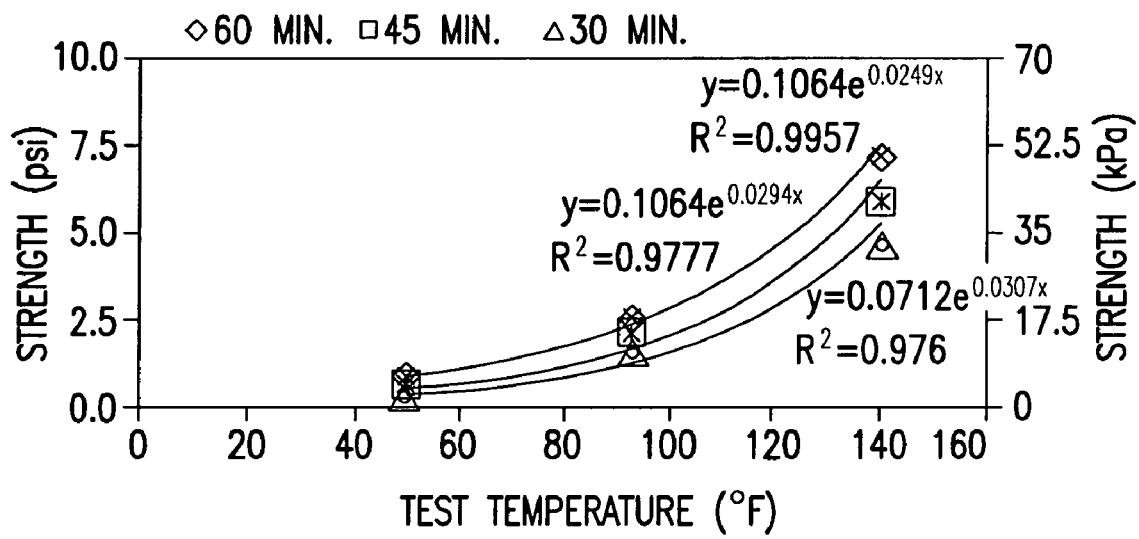
Figure 10C:
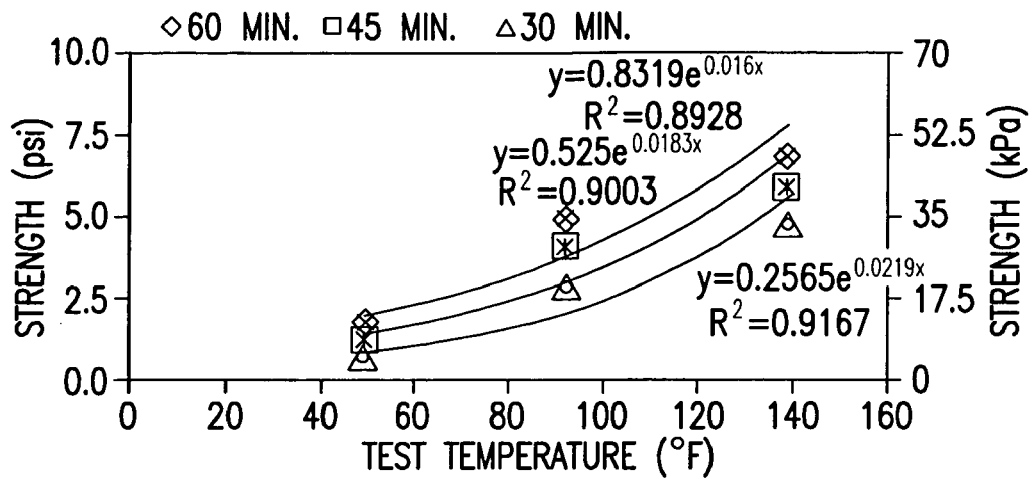
Figure 10D:
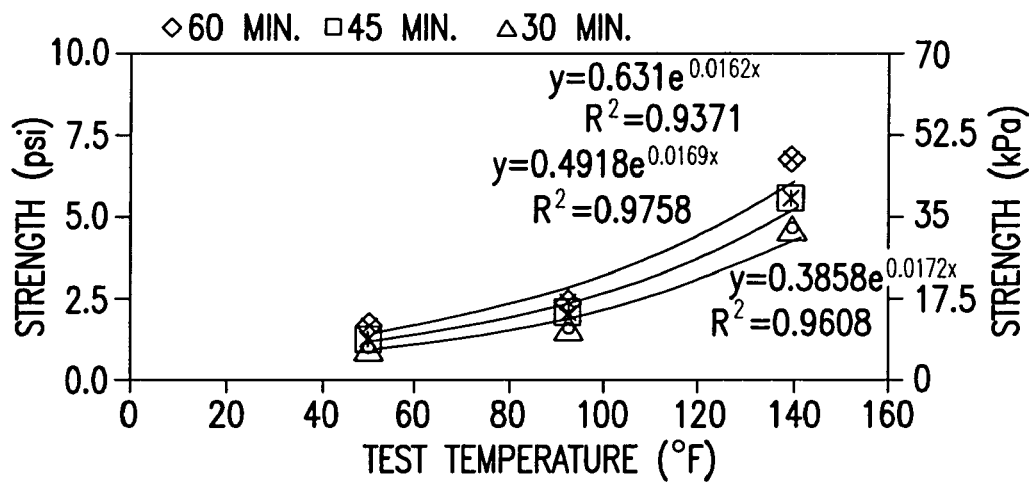
Figure 10E:
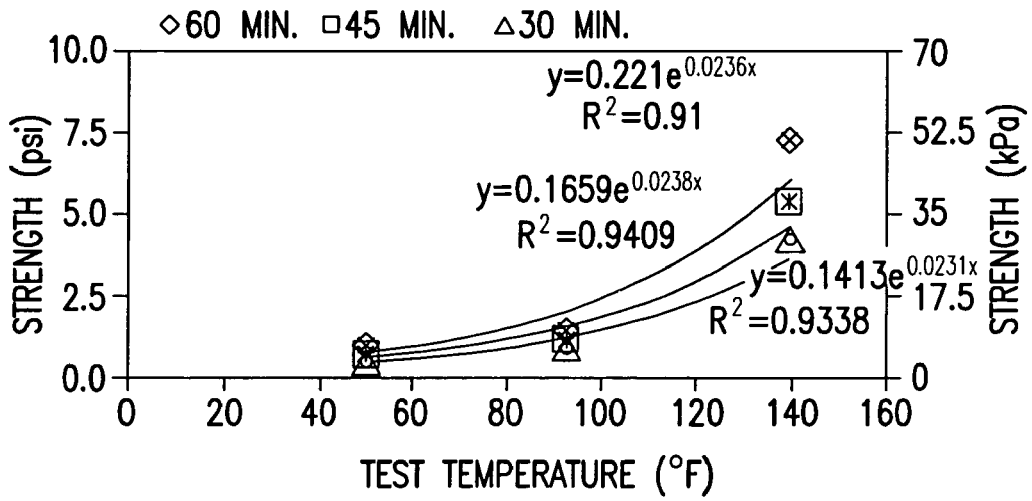
Figure 13:
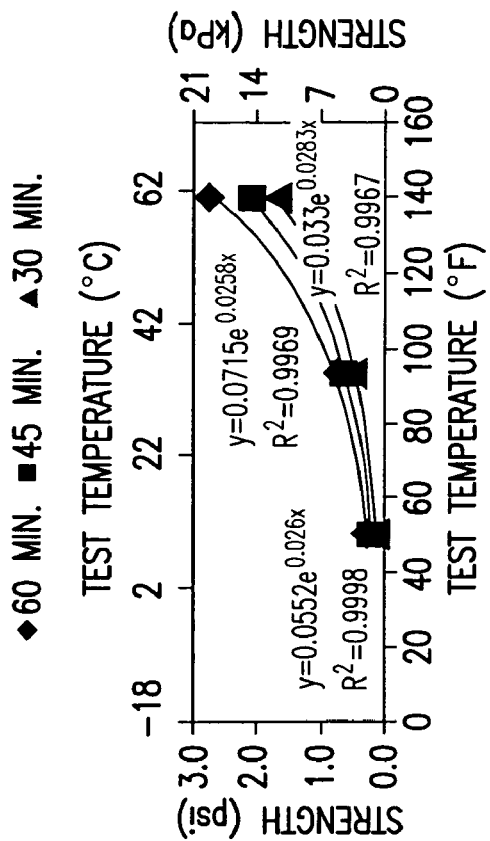
FIG. 13 shows a plot of test results in accordance with embodiments of the disclosure.
Figure 14:
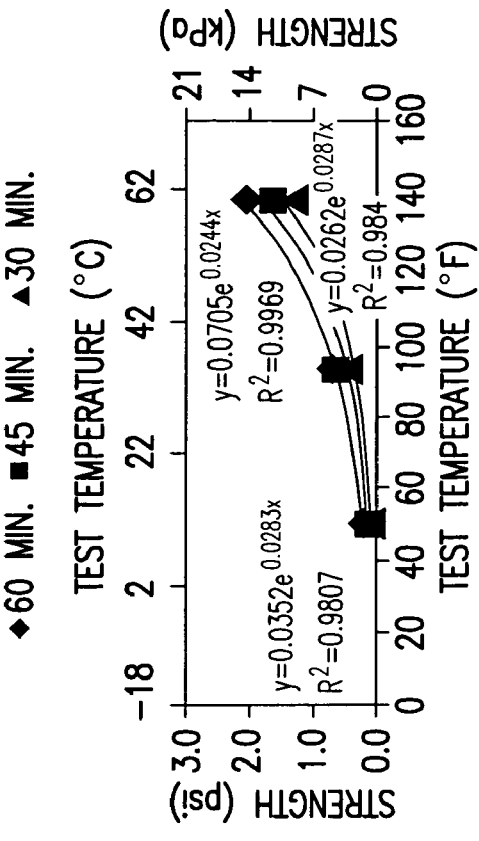
FIG. 14 shows a plot of test results in accordance with embodiments of the disclosure.
Figure 11:
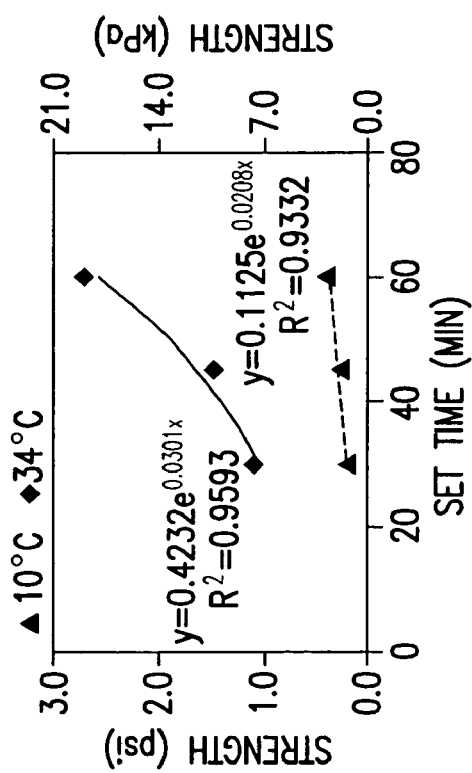
FIG. 11 shows a plot of test results for a direct shear device in accordance with embodiments of the disclosure.
Figure 12:
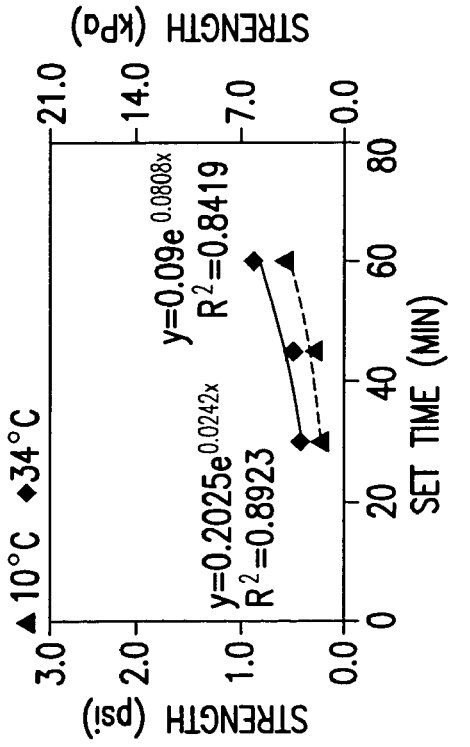
FIG. 12 shows a plot of test results for a direct shear device in accordance with embodiments of the disclosure.

In another embodiment, an apparatus 800 for testing the pavement surface may include a shaft 806 coupled to a contact plate 804, as shown in FIG. 9. The contact plate 104 may include a flexible adhesive layer for adhering the contact plate to the tack coat. A load may be applied to one distal end of the shaft 806 to help the contact plate conform to the tack coat layer. The apparatus 800 may also include a dial gauge 808 for measuring the load required to pull the contact plate from the tack coat layer.

In operation, apparatus 100 works as follows. Upon applying a tack coat to a pavement surface, apparatus 100 may be placed on the tack coat to measure the adhesive quality of the tack coat. Contact plate 104 may adhere and conform to the shape of the pavement surface for added stability. In some embodiments, a load may be applied to contact plate 104 to aid the contact plate to conform to the shape of the surface. Upon setting contact plate 104 in place, torque wrench 600 may rotate in one direction (e.g., rotated counter-clock wise) to pull off contact plate 104 from the pavement surface and the force measuring device 602 may register the force it took to lift the contact plate.

It is noted that the dimensions provided in all the Figures are an illustrative embodiment. Particularly, the dimensions in the Figures show that the apparatus is a portable device, capable of being used in the field for testing. Other dimensions can also be used.

EXAMPLES

Specific embodiments of the invention will now be further described by the following, nonlimiting examples which will serve to illustrate in some detail various features. The following examples are included to facilitate an understanding of ways in which the invention may be practiced. It should be appreciated that the examples which follow represent embodiments discovered to function well in the practice of the invention, and thus can be considered to constitute preferred modes for the practice of the invention. However, it should be appreciated that many changes can be made in the exemplary embodiments which are disclosed while still obtaining like or similar result without departing from the spirit and scope of the invention. Accordingly, the examples should not be construed as limiting the scope of the invention.

Example 1

Compiled Data of Field-Test Conducted in Different Environmental Conditions for an Apparatus with Support Members Positioned in a Tripod Configuration An apparatus with support members positioned in a tripod configuration weighs about 10.4 kg and can be easily leveled with the help of pivoting feet. It has a weight key on the top, which provides stability when loads are placed on the top. A 9.5 mm nut fits a 9.5 mm torque wrench, which is used to pull the contact plate up from the tack-coated surface. A 0–18 N-m torque wrench is used for measuring pull-off torque that can be converted into pull-off strength. A contact plate that can conform to the rough pavement surface is also developed.

The device consists of a 127 mm diameter aluminum contact test plate. A 127 mm² double-sided tape is used and attached to the aluminum contact plate and 127 mm² moisture bearing foam is placed over the tape. The advantage of the moisture bearing foam is that it can be easily peeled off the double sided tape and four to five tests can be performed before the adhesive layer (double sided tape) needs replacement.

The device consists of three gears namely a worm, a worm gear, (also acts as a pinion) and a rack arrangement. The worm and the worm gear are used to transfer the force that is being applied in the form of a hand cranking (torque) in vertical direction to which translates into vertical force.

To perform tests in the field, a desired amount of tack coat is placed on top of the pavement surface. After tack coat application, the tack coat is allowed to set for a specified period of time. After specified set time, the apparatus is placed on the tack-coated surface. The torque wrench is rotated clockwise until the contact plate is firmly set on the tack-coated pavement. The loads are placed on the load rack (at the top of the device) for specified time prior to testing. In the end, the loads are removed and the torque wrench is attached to the 9.5 mm nut and rotated in the counter clockwise direction to detach the contact plate from the tack-coated pavement. The torque (T) required to detach the contact plate from the tack coated pavement is recorded in N-m. The torque (T) is then converted to the load using a calibration factor. The breaking load is then converted to stress for evaluation of tack coats. The tests can be performed in the laboratory by applying tack coat on the two aluminum plates mentioned previously, which are maintained at a specified temperature.

Environmental contributions, such as the temperature of the pavement and the ambient air may affect the quality of the tack coat layer. The following tables compile a plurality of data based on the time of day the test was conducted, the temperature of the pavement and ambient air, and how different loads applied to the plate of apparatus alter the results. Further, the results also contemplate a tack coat diluted with water (for allowing the tack coat to flow across the existing pavement) to determine if the diluted tack coat would increase the set time, i.e., the time period required for the tack coat to change from a liquid state to a solid state. The application rate was also considered. The application rate measured in gallons per squared yard may be proportional to the thickness of the tack coat.

The compiled results report a mean value (Mean), and the standard deviation (Std Dev) was reported for the average of the three readings performed by single operator for the particular dilution, set time, and load. The coefficient of variation (COV) reported the ratio of the standard deviation and the mean.

TABLE 1

| Dilution | Application Rate (gal/yd$^2$) | Set Time (mins) | Load (lbs) | Mean (psi) | Std Dev (psi) | COV (%) |
|---|---|---|---|---|---|---|
| None | 0.04 gal/yd$^2$ | 20 | 20 | 0.43 | 0.03 | 8 |
| | Time - 7 AM | | 30 | 0.56 | 0.07 | 12 |
| | Air Temp (° F.) - 47.2 | | 40 | 0.92 | 0.07 | 7.4 |
| | Pavement Temp | 30 | 20 | 0.6 | 0.07 | 11.26 |
| | (° F.) - 44.1 | | 30 | 0.92 | 0.07 | 7.41 |
| | | | 40 | 1.15 | 0.07 | 5.9 |
| | 0.1 gal/yd$^2$ | 20 | 20 | 0.48 | 0.04 | 7.55 |
| | Time - 7 AM | | 30 | 0.84 | 0.07 | 8.1 |
| | Air Temp (° F.) - 49.1 | | 40 | 1.19 | 0.14 | 11.4 |
| | Pavement Temp | 30 | 20 | 0.84 | 0.07 | 8.1 |
| | (° F.) - 41 | | 30 | 1.04 | 0.07 | 6.57 |
| | | | 40 | 1.43 | 0.14 | 9.52 |

TABLE 2

| Dilution | Application Rate (gal/yd$^2$) | Set Time (mins) | Load (lbs) | Mean (psi) | Std Dev (psi) | COV (%) |
|---|---|---|---|---|---|---|
| 50/50 | 0.04 gal/yd$^2$ | 20 | 20 | 0.33 | 0.7 | 20.67 |
| | Time - 7 AM | | 30 | 0.37 | 0.7 | 18.47 |
| | Air Temp (° F.) - 52 | | 40 | 0.49 | 0.7 | 13.99 |
| | Pavement Temp | 30 | 20 | 0.37 | 0.7 | 18.47 |
| | (° F.) - 49.6 | | 30 | 0.45 | 0.7 | 15.22 |
| | | | 40 | 0.6 | 0.7 | 11.26 |
| | 0.1 gal/yd$^2$ | 20 | 20 | 0.37 | 0.7 | 18.47 |
| | Time - 7 AM | | 30 | 0.45 | 0.7 | 15.22 |
| | Air Temp (° F.) - 54.5 | | 40 | 0.6 | 0.7 | 11.26 |
| | Pavement Temp | 30 | 20 | 0.41 | 0 | 0 |
| | (° F.) - 49.3 | | 30 | 0.49 | 0.7 | 13.99 |
| | | | 40 | 0.68 | 0.7 | 9.97 |

TABLE 3

| Dilution | Application Rate (gal/yd$^2$) | Set Time (mins) | Load (lbs) | Mean (psi) | Std Dev (psi) | COV (%) |
|---|---|---|---|---|---|---|
| None | 0.04 gal/yd$^2$ | 20 | 20 | 0.49 | 0.07 | 13.99 |
| | Time - 7 AM | | 30 | 0.72 | 0.07 | 9.42 |
| | Air Temp (° F.) - 57 | | 40 | 1.08 | 0.07 | 6.33 |
| | Pavement Temp | 30 | 20 | 0.72 | 0.07 | 9.42 |
| | (° F.) - 61 | | 30 | 1.08 | 0.07 | 6.33 |
| | | | 40 | 1.31 | 0.07 | 5.19 |
| | 0.1 gal/yd$^2$ | 20 | 20 | 0.8 | 0.07 | 8.5 |
| | Time - 3 PM | | 30 | 1.19 | 0.07 | 5.7 |
| | Air Temp (° F.) - 63.9 | | 40 | 1.43 | 1.14 | 9.52 |
| | Pavement Temp | 30 | 20 | 1.04 | 0.07 | 6.57 |
| | (° F.) - 59.2 | | 30 | 1.39 | 0.07 | 4.9 |
| | | | 40 | 1.74 | 0.07 | 3.9 |

TABLE 4

| Dilution | Application Rate (gal/yd$^2$) | Set Time (mins) | Load (lbs) | Mean (psi) | Std Dev (psi) | COV (%) |
|---|---|---|---|---|---|---|
| 50/50 | 0.04 gal/yd$^2$ | 20 | 20 | 0.37 | 0.07 | 18.47 |
| | Time - 3 PM | | 30 | 0.49 | 0.07 | 13.99 |
| | Air Temp (° F.) - 69 | | 40 | 0.64 | 0 | 0 |
| | Pavement Temp | 30 | 20 | 0.41 | 0 | 0 |
| | (° F.) - 66 | | 30 | 0.56 | 0.07 | 12.05 |
| | | | 40 | 0.72 | 0.07 | 9.42 |
| | 0.1 gal/yd$^2$ | 20 | 20 | 0.45 | 0.07 | 15.22 |
| | Time - 3 PM | | 30 | 0.56 | 0.07 | 12.05 |
| | Air Temp (° F.) - 65.2 | | 40 | 0.68 | 0.07 | 9.97 |
| | Pavement Temp | 30 | 20 | 0.49 | 0.07 | 13.99 |
| | (° F.) - 62.3 | | 30 | 0.6 | 0.07 | 11.26 |
| | | | 40 | 0.84 | 0.07 | 8.1 |

TABLE 5

| Dilution | Application Rate (gal/yd$^2$) | Set Time (mins) | Load (lbs) | Mean (psi) | Std Dev (psi) | COV (%) |
|---|---|---|---|---|---|---|
| None | 0.04 gal/yd$^2$ | 20 | 20 | 0.49 | 0.07 | 14 |
| | Time - 7AM | | 30 | 0.6 | 0.07 | 11.3 |
| | Air Temp (° F.) - 45.3 | | 40 | 1 | 0 | 0 |
| | Pavement Temp | 30 | 20 | 0.68 | 0.07 | 9.97 |
| | (° F.) - 40.2 | | 30 | 0.96 | 0.07 | 7.1 |
| | | | 40 | 1.19 | 0.07 | 5.7 |
| | 0.1 gal/yd$^2$ | 20 | 20 | 0.54 | 0.09 | 17.24 |
| | Time - 7 AM | | 30 | 0.92 | 0.07 | 7.41 |
| | Air Temp (° F.) - 45.3 | | 40 | 1.27 | 0.07 | 5.35 |
| | Pavement Temp | 30 | 20 | 0.88 | 0 | 0 |
| | (° F.) - 40.2 | | 30 | 1.08 | 0.07 | 6.33 |
| | | | 40 | 1.51 | 0.14 | 9.03 |

TABLE 6

| Dilution | Application Rate (gal/yd$^2$) | Set Time (mins) | Load (lbs) | Mean (psi) | Std Dev (psi) | COV (%) |
|---|---|---|---|---|---|---|
| 50/50 | 0.04 gal/yd$^2$ | 20 | 20 | 0.37 | 0.07 | 18.47 |
| | Time - 7 AM | | 30 | 0.41 | 0 | 0 |
| | Air Temp (° F.) - 44.1 | | 40 | 0.49 | 0.07 | 13.99 |
| | Pavement Temp | 30 | 20 | 0.41 | 0 | 0 |
| | (° F.) - 41 | | 30 | 0.45 | 0.07 | 15.22 |
| | | | 40 | 0.68 | 0.07 | 9.97 |
| | 0.1 gal/yd$^2$ | 20 | 20 | 0.45 | 0.07 | 15.22 |
| | Time - 7 AM | | 30 | 0.6 | 0.07 | 11.26 |
| | Air Temp (° F.) - 44.1 | | 40 | 0.8 | 0.07 | 8.5 |
| | Pavement Temp | 30 | 20 | 0.56 | 0.07 | 12.07 |
| | (° F.) - 41 | | 30 | 0.68 | 0.07 | 9.97 |
| | | | 40 | 0.88 | 0 | 0 |

TABLE 7

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.6 | 0.07 | 11.26 |
| | Time - 3 PM | | 30 | 0.72 | 0.07 | 9.42 |
| | Air Temp (° F.) - 69.4 | | 40 | 1.15 | 0.07 | 5.9 |
| | Pavement Temp | 30 | 20 | 0.84 | 0.07 | 8.1 |
| | (° F.) - 63.2 | | 30 | 1.19 | 0.07 | 5.7 |
| | | | 40 | 1.43 | 0.07 | 4.76 |
| | 0.1 gal/yd² | 20 | 20 | 0.84 | 0.07 | 8.1 |
| | Time - 3 PM | | 30 | 1.27 | 0.07 | 5.35 |
| | Air Temp (° F.) - 69.4 | | 40 | 1.43 | 0.07 | 4.76 |
| | Pavement Temp | 30 | 20 | 1.15 | 0.07 | 5.9 |
| | (° F.) - 63.2 | | 30 | 1.51 | 0.14 | 9.03 |
| | | | 40 | 2.02 | 0.07 | 3.37 |

TABLE 8

| Dilution | Application Rate (gal/yd²) | Set Time (mins) | Load (lbs) | Mean (psi) | Std Dev (psi) | COV (%) |
|---|---|---|---|---|---|---|
| 50/50 | 0.04 gal/yd² | 20 | 20 | 0.45 | 0.07 | 15.22 |
| | Time - 3 PM | | 30 | 0.56 | 0.07 | 12.05 |
| | Air Temp (° F.) - 79 | | 40 | 0.72 | 0.07 | 9.42 |
| | Pavement Temp | 30 | 20 | 0.49 | 0.07 | 13.99 |
| | (° F.) - 75 | | 30 | 0.6 | 0.07 | 11.26 |
| | | | 40 | 0.8 | 0.07 | 8.5 |
| | 0.1 gal/yd² | 20 | 20 | 0.49 | 0.07 | 13.99 |
| | Time - 3 PM | | 30 | 0.64 | 0.12 | 18.32 |
| | Air Temp (° F.) - 79 | | 40 | 0.84 | 0.07 | 8.1 |
| | Pavement Temp | 30 | 20 | 0.56 | 0.07 | 12.05 |
| | (° F.) - 75 | | 30 | 0.72 | 0.07 | 9.42 |
| | | | 40 | 0.92 | 0.07 | 7.41 |

TABLE 9

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.41 | 0 | 0 |
| | Time - 7 AM | | 30 | 0.49 | 0.07 | 14 |
| | Air Temp (° F.) - 54 | | 40 | 0.68 | 0.07 | 10 |
| | Pavement Temp | 30 | 20 | 0.49 | 0.07 | 13.99 |
| | (° F.) - 43 | | 30 | 0.6 | 0.07 | 11.26 |
| | | | 40 | 0.84 | 0.07 | 8.1 |
| | 0.1 gal/yd² | 20 | 20 | 0.68 | 0.07 | 9.97 |
| | Time - 7 AM | | 30 | 0.8 | 0.07 | 8.5 |
| | Air Temp (° F.) - 54 | | 40 | 1.04 | 0.07 | 6.57 |
| | Pavement Temp | 30 | 20 | 0.8 | 0.07 | 8.5 |
| | (° F.) - 43 | | 30 | 0.92 | 0.07 | 7.41 |
| | | | 40 | 1.11 | 0 | 0 |

TABLE 10

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 1.9 | 0.14 | 7.16 |
| | Time - 3 PM | | 30 | 2.45 | 0.14 | 5.55 |
| | Air Temp (° F.) - 74 | | 40 | 2.92 | 0.14 | 4.66 |
| | Pavement Temp | 30 | 20 | 2.14 | 0.14 | 6.37 |
| | (° F.) - 83 | | 30 | 2.69 | 0.14 | 5.07 |
| | | | 40 | 3.08 | 0.14 | 4.42 |
| | 0.1 gal/yd² | 20 | 20 | 2.21 | 0.14 | 6.14 |
| | Time - 3 PM | | 30 | 2.84 | 0.14 | 4.79 |
| | Air Temp (° F.) - 74 | | 40 | 3.31 | 0.14 | 4.11 |
| | Pavement Temp | 30 | 20 | 2.41 | 0.14 | 4.89 |
| | (° F.) - 83 | | 30 | 3.16 | 0.14 | 4.31 |
| | | | 40 | 3.55 | 0.14 | 3.83 |

As seen from the Tables listed above and referring to FIGS. 10A through 10E, the apparatus provides an on-site analysis of the quality of the tack coat layer based on the surrounding environment the tack-coat layer was applied. In general the test, including taking multiple readings to compile an average, was completed in 15 minutes or less.

Example 2

Compiled Data of Field-Test Conducted in Different Environmental Conditions for an Apparatus Without Support Members The following tables compile a plurality of data based on the time of day the test was conducted, the temperature of the pavement and ambient air, and how different loads applied to the plate of apparatus alter results. The tests were performed under similar conditions as Example 1.

TABLE 11

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.31 | 0 | 0 |
| | Time - 7 AM | | 30 | 0.42 | 0.03 | 6.93 |
| | Air Temp (° F.) - 47.2 | | 40 | 0.63 | 0.03 | 4.68 |
| | Pavement Temp | 30 | 20 | 0.34 | 0.03 | 8.66 |
| | (° F.) - 44.1 | | 30 | 0.49 | 0.03 | 5.97 |
| | | | 40 | 0.73 | 0.03 | 4.03 |
| | 0.1 gal/yd² | 20 | 20 | 0.44 | 0.03 | 6.66 |
| | Time - 7 AM | | 30 | 0.58 | 0.03 | 5.09 |
| | Air Temp (° F.) - 49.1 | | 40 | 0.78 | 0.03 | 7.53 |
| | Pavement Temp | 30 | 20 | 0.48 | 0.03 | 6.19 |
| | (° F.) - 41 | | 30 | 0.68 | 0.06 | 8.66 |
| | | | 40 | 0.85 | 0.06 | 6.93 |

TABLE 12

| Dilution | Application Rate (gal/yd²) | Set Time (mins) | Load (lbs) | Mean (psi) | Std Dev (psi) | COV (%) |
|---|---|---|---|---|---|---|
| 50/50 | 0.04 gal/yd² | 20 | 20 | 0.31 | 0 | 0 |
| | Time - 7 AM | | 30 | 0.32 | 0.03 | 9.12 |
| | Air Temp (° F.) - 52 | | 40 | 0.37 | 0.03 | 7.87 |
| | Pavement Temp | 30 | 20 | 0.31 | 0 | 0 |
| | (° F.) - 49.7 | | 30 | 0.34 | 0.03 | 8.66 |
| | | | 40 | 0.39 | 0.03 | 7.53 |
| | 0.1 gal/yd² | 20 | 20 | 0.31 | 0 | 0 |
| | Time - 7 AM | | 30 | 0.34 | 0.03 | 8.66 |
| | Air Temp (° F.) - 54.5 | | 40 | 0.39 | 0.03 | 7.53 |
| | Pavement Temp | 30 | 20 | 0.31 | 0 | 0 |
| | (° F.) - 49.3 | | 30 | 0.34 | 0.03 | 8.66 |
| | | | 40 | 0.43 | 0.03 | 5.88 |

TABLE 13

| | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.39 | 0.03 | 7.53 |
| | Time - 3 PM | | 30 | 0.48 | 0.03 | 6.19 |
| | Air Temp (° F.) - 57 | | 40 | 0.73 | 0.03 | 4.03 |
| | Pavement Temp (° F.) - 61 | 30 | 20 | 0.39 | 0.03 | 7.53 |
| | | | 30 | 0.59 | 0.03 | 4.95 |
| | | | 40 | 0.9 | 0.03 | 3.27 |
| | 0.1 gal/yd² | 20 | 20 | 0.73 | 0.03 | 4.03 |
| | Time - 3 PM | | 30 | 0.93 | 0.03 | 3.15 |
| | Air Temp (° F.) - 63.9 | | 40 | 1.17 | 0.05 | 4.35 |
| | Pavement Temp (° F.) - 59.2 | 30 | 20 | 0.86 | 0.01 | 1.71 |
| | | | 30 | 1.14 | 0.06 | 5.17 |
| | | | 40 | 1.41 | 0.03 | 2.09 |

TABLE 14

| Dilution | Application Rate (gal/yd²) | Set Time (mins) | Load (lbs) | Mean (psi) | Std Dev (psi) | COV (%) |
|---|---|---|---|---|---|---|
| 50/50 | 0.04 gal/yd² | 20 | 20 | 0.32 | 0.03 | 9.12 |
| | Time - 3 PM | | 30 | 0.44 | 0.03 | 6.66 |
| | Air Temp (° F.) - 69 | | 40 | 0.49 | 0.03 | 5.97 |
| | Pavement Temp (° F.) - 66 | 30 | 20 | 0.37 | 0.03 | 7.87 |
| | | | 30 | 0.48 | 0.03 | 6.19 |
| | | | 40 | 0.59 | 0.03 | 4.95 |
| | 0.1 gal/yd² | 20 | 20 | 0.39 | 0.03 | 7.53 |
| | Time - 3 PM | | 30 | 0.49 | 0.03 | 5.97 |
| | Air Temp (° F.) - 65.2 | | 40 | 0.65 | 0.03 | 4.56 |
| | Pavement Temp (° F.) - 62.3 | 30 | 20 | 0.41 | 0 | 0 |
| | | | 30 | 0.63 | 0.03 | 4.68 |
| | | | 40 | 0.78 | 0.03 | 3.77 |

TABLE 15

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.31 | 0 | 0 |
| | Time - 7 AM | | 30 | 0.44 | 0.03 | 6.66 |
| | Air Temp (° F.) - 45.3 | | 40 | 0.68 | 0.03 | 4.33 |
| | Pavement Temp (° F.) - 40.2 | 30 | 20 | 0.37 | 0.03 | 7.87 |
| | | | 30 | 0.54 | 0.03 | 5.41 |
| | | | 40 | 0.8 | 0.03 | 3.69 |
| | 0.1 gal/yd² | 20 | 20 | 0.48 | 0.03 | 6.19 |
| | Time - 7 AM | | 30 | 0.63 | 0.03 | 4.68 |
| | Air Temp (° F.) - 45.3 | | 40 | 0.75 | 0.03 | 3.94 |
| | Pavement Temp (° F.) - 40.2 | 30 | 20 | 0.51 | 0 | 0 |
| | | | 30 | 0.7 | 0.03 | 4.22 |
| | | | 40 | 0.95 | 0.06 | 6.19 |

TABLE 16

| Dilution | Application Rate (gal/yd²) | Set Time (mins) | Load (lbs) | Mean (psi) | Std Dev (psi) | COV (%) |
|---|---|---|---|---|---|---|
| 50/50 | 0.04 gal/yd² | 20 | 20 | 0.31 | 0 | 0 |
| | Time - 7 AM | | 30 | 0.34 | 0.03 | 8.66 |
| | Air Temp (° F.) - 44.1 | | 40 | 0.39 | 0.03 | 7.53 |
| | Pavement Temp (° F.) - 41 | 30 | 20 | 0.32 | 0.03 | 9.12 |
| | | | 30 | 0.35 | 0.01 | 4.22 |
| | | | 40 | 041 | 0.05 | 12.5 |
| | 0.1 gal/yd² | 20 | 20 | 0.31 | 0 | 0 |
| | Time - 7 AM | | 30 | 0.37 | 0.03 | 7.87 |
| | Air Temp (° F.) - 44.1 | | 40 | 0.41 | 0 | 0 |
| | Pavement Temp (° F.) - 41 | 30 | 20 | 0.31 | 0 | 0 |
| | | | 30 | 0.37 | 0.03 | 7.87 |
| | | | 40 | 0.44 | 0.03 | 6.66 |

TABLE 17

| | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.42 | 0.03 | 6.93 |
| | Time - 3 PM | | 30 | 0.54 | 0.06 | 10.83 |
| | Air Temp (° F.) - 69.4 | | 40 | 0.78 | 0.06 | 7.53 |
| | Pavement Temp (° F.) - 63.2 | 30 | 20 | 0.44 | 0.03 | 6.66 |
| | | | 30 | 0.65 | 0.03 | 4.56 |
| | | | 40 | 0.95 | 0.03 | 3.09 |
| | 0.1 gal/yd² | 20 | 20 | 0.88 | 0.06 | 6.66 |
| | Time - 3 PM | | 30 | 0.97 | 0.05 | 5.26 |
| | Air Temp (° F.) - 69.4 | | 40 | 1.19 | 0.06 | 4.95 |
| | Pavement Temp (° F.) - 63.2 | 30 | 20 | 0.99 | 0.06 | 5.97 |
| | | | 30 | 1.19 | 0.06 | 4.95 |
| | | | 40 | 1.53 | 1 | 6.67 |

TABLE 18

| Dilution | Application Rate (gal/yd²) | Set Time (mins) | Load (lbs) | Mean (psi) | Std Dev (psi) | COV (%) |
|---|---|---|---|---|---|---|
| 50/50 | 0.04 gal/yd² | 20 | 20 | 0.34 | 0.03 | 8.66 |
| | Time - 3 PM | | 30 | 0.46 | 0.05 | 11.11 |
| | Air Temp (° F.) - 79 | | 40 | 0.54 | 0.03 | 5.41 |
| | Pavement Temp (° F.) - 75 | 30 | 20 | 0.41 | 0.05 | 12.5 |
| | | | 30 | 0.49 | 0.03 | 5.97 |
| | | | 40 | 0.63 | 0.03 | 4.68 |
| | 0.1 gal/yd² | 20 | 20 | 0.42 | 0.03 | 6.93 |
| | Time - 3 PM | | 30 | 0.53 | 0.03 | 5.59 |
| | Air Temp (° F.) - 79 | | 40 | 0.68 | 0.03 | 4.33 |
| | Pavement Temp (° F.) - 75 | 30 | 20 | 0.44 | 0.03 | 6.66 |
| | | | 30 | 0.65 | 0.03 | 4.56 |
| | | | 40 | 0.83 | 0.03 | 3.53 |

TABLE 19

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 0.34 | 0.03 | 8.66 |
| | Time - 7 AM | | 30 | 0.42 | 0.03 | 6.93 |
| | Air Temp (° F.) - 54 | | 40 | 0.49 | 0.03 | 5.97 |
| | Pavement Temp (° F.) - 43 | 30 | 20 | 0.36 | 0 | 0 |
| | | | 30 | 0.44 | 0.03 | 6.66 |
| | | | 40 | 0.58 | 0.03 | 5.09 |
| | 0.1 gal/yd² | 20 | 20 | 0.41 | 0 | 0 |
| | Time - 7 AM | | 30 | 0.48 | 0.03 | 6.19 |
| | Air Temp (° F.) - 54 | | 40 | 0.59 | 0.03 | 4.95 |
| | Pavement Temp (° F.) - 43 | 30 | 20 | 0.42 | 0.03 | 6.93 |
| | | | 30 | 0.54 | 0.03 | 5.41 |
| | | | 40 | 0.65 | 0.03 | 4.56 |

TABLE 20

| Dilution | Application Rate (gal/yd²) | Set Time (mins) | Load (lbs) | Mean (psi) | Std Dev (psi) | COV (%) |
|---|---|---|---|---|---|---|
| None | 0.04 gal/yd² | 20 | 20 | 1.00 | 0.08 | 7.77 |
| | Time - 7AM | | 30 | 1.12 | 0.10 | 9.09 |
| | Air Temp (° F.) - 74 | | 40 | 1.22 | 0.10 | 8.33 |
| | Pavement Temp (° F.) - 83 | 30 | 20 | 1.05 | 0.06 | 5.59 |
| | | | 30 | 1.15 | 0.06 | 5.09 |
| | | | 40 | 1.29 | 0.06 | 4.56 |
| | 0.1 gal/yd² | 20 | 20 | 1.26 | 0.06 | 4.68 |
| | Time - 7 AM | | 30 | 1.48 | 0.05 | 3.45 |
| | Air Temp (° F.) - 74 | | 40 | 1.78 | 0.09 | 4.95 |
| | Pavement Temp (° F.) - 83 | 30 | 20 | 1.36 | 0.06 | 4.33 |
| | | | 30 | 1.73 | 0.10 | 5.88 |
| | | | 40 | 2.14 | 0.10 | 4.76 |

Example 3

Performance Comparison Between a Direct Shear Apparatus and an Apparatus with Support Members Positioned in a Tripod Configuration in the Laboratory In geotechnical engineering, a direct shear (DS) device is commonly used for the measurements of shear strength of the soil. The tests are typically performed by varying the normal stress, and Mohr-Coulomb failure criterion is used to obtain shear strength. A test performed in the direct shear mode could provide information about the quality of the tack coat as well as frictional strength offered by different mix types. In the case of tack coat testing, the test would require a longer testing time and would not be a practical field test.

To perform tests in the field, a pull off test (using apparatus 100 in FIG. 1) could be performed rather than shear strength. The advantage of the pull off test would be that the effect of frictional component is not included. The basic assumption is that the tensile strength measured from the pull-off tests is similar to the cohesive strength expected to be provided by the tack coat. Therefore, a direct shear test setup was modified and a pull-off test device was developed to verify the assumption.

A laboratory evaluation of a direct shear device and an apparatus, such as apparatus 100 of FIG. 1, hereinafter referred to as a pull-off device ("POD") using parameters presented in Table 21.

TABLE 21

| Parameters | Tack Coat Type | | | |
| --- | --- | --- | --- | --- |
| | CSS-1h | CSS-1 | SS-1h | PG64-22 |
| Dilution level | None | None | None | None |
| Set Time (min) | 30 | 30 | 30 | 30 |
| | 45 | 45 | 45 | 45 |
| | 60 | 60 | 60 | 60 |
| Test Temperature (° C.) | 10 | 10 | 10 | 10 |
| | 34 | 34 | 34 | 34 |
| | 60 | 60 | 60 | 60 |
| Load (kg) | 18 | 18 | 18 | 18 |
| Loading Time (min) | 10 | 10 | 10 | 10 |
| Normal stress (kPa) | 34.4 | 34.4 | 34.4 | 34.4 |
| | 68.9 | 68.9 | 68.9 | 68.9 |
| | 103.3 | 103.3 | 103.3 | 103.3 |
| Residual Application Rate (l/m$^2$) | 0.18 | 0.18 | 0.18 | 0.18 |

In the laboratory, two aluminum plates were fabricated for laboratory testing. One of the plates is a thick solid plate with the dimensions of 419 mm by 368 mm by 6.35 mm. The other plate is a thin plate with the dimensions of 393.7 mm by 305 mm by 0.787 mm and has a hole of 127 mm diameter in the center. The plate with the hole in center is placed on top of the solid plate. This allows the placement of tack coat in the circular area.

To perform pull-off tests described above, a desired amount of tack coat was placed on top of the aluminum plate of the POD, and was maintained at a specified temperature. After the specified set time, the apparatus is placed on top of the aluminum plates. The torque wrench is rotated clockwise until the contact plate is firmly set on the tack-coated pavement. Loads of 18 kg are placed on the load rack (at the top of the device) for ten minutes prior to testing. The selection of 18 kg load was based on the results of Example 1, which identified that better repeatability could be obtained at this load level. After 10 minutes, the loads are removed and the torque wrench is rotated in the counter clockwise direction to detach the contact plate from the tack-coated pavement. The torque (T) required to detach the contact plate from the tack coated pavement is recorded in N-m. The torque (T) is then converted to the load using a calibration factor. The breaking load is then converted to stress for evaluation of tack coats.

To perform direct shear (DS) tests using a direct shear device known in the art, the asphalt concrete or aluminum specimens were placed inside an oven maintained at specified temperature. The tack coat to be tested was placed on one of the specimen. The other specimen was then placed on top of the tack coated specimen after specified set time. After set time, the load of 18 kg was maintained for 10 minutes. The specimens were then tested in the DS device at different temperature and normal stress. The normal stresses applied are 5, 10, and 15 psi. A relationship between the strength, cohesion, and friction was developed for each tack coat type.

a. Test Results

The DS test results, shown in Table 22 and 23, are compared to the test results shown in Table 24 for the apparatus with support members. The test results shown in Table 22 show the cohesive as well as frictional resistance measured by the DS test device for CSS-1h tack coat while Table 23 shows only cohesive strength for the tack coat types.

The test results show that the cohesive strength depends on the application rate, set time, and test temperature. The difference is the POD is independent of the surface tested, and therefore, can be used in the field to identify the quality of a tack coat.

TABLE 22

| Test | | Aluminum Specimen | | |
| --- | --- | --- | --- | --- |
| Temperature, ° C. | Set Time, min | Friction Angle, (degrees) | Cohesion, psi | Total Strength, psi |
| 60 | 60 | 28.8 | 4.70 | 5.77 |
| | 45 | 28.3 | 2.05 | 3.14 |
| | 30 | 26.6 | 1.10 | 2.11 |
| 34 | 60 | 2.1 | 2.71 | 2.78 |
| | 45 | 4.2 | 1.47 | 1.61 |
| | 30 | 4.5 | 1.10 | 1.25 |
| 10 | 60 | 12.5 | 0.41 | 0.86 |
| | 45 | 11.3 | 0.26 | 0.66 |
| | 30 | 10.4 | 0.22 | 0.59 |

TABLE 23

| Test Temp., ° C. | Set Time, min | CSS-1h Avg. Str., psi | CSS-1 Avg. Str., psi | PG64-22 Avg. Str., psi | SS-1h Avg. Str., psi |
| --- | --- | --- | --- | --- | --- |
| 34 | 60 | 2.71 | 1.52 | 1.40 | 0.93 |
| | 45 | 1.47 | 1.2 | 1.20 | 0.52 |
| | 30 | 1.10 | 0.66 | 0.93 | 0.45 |
| 10 | 60 | 0.41 | 0.4 | 0.96 | 0.62 |
| | 45 | 0.26 | 0.2 | 0.43 | 0.28 |
| | 30 | 0.22 | 0.15 | 0.23 | 0.25 |

TABLE 24

| Test Temp., ° C. | Set Time, min | CSS-1h Avg. Str., psi | CSS-1h COV, % | CSS-1 Avg. Str., psi | CSS-1 COV, % | PG64-22 Avg. Str., psi | PG64-22 COV, % | SS-1h Avg. Str., psi | SS-1h COV, % |
|---|---|---|---|---|---|---|---|---|---|
| 60 | 60 | 2.74 | 7.37 | 2.07 | 7.37 | 1.94 | 3.48 | 2.07 | 3.25 |
|  | 45 | 2.07 | 6.51 | 1.67 | 6.51 | 1.67 | 4.04 | 1.59 | 4.21 |
|  | 30 | 1.67 | 6.26 | 1.34 | 6.26 | 1.34 | 5.07 | 1.20 | 5.64 |
| 34 | 60 | 0.73 | 9.32 | 0.73 | 9.32 | 1.40 | 4.82 | 0.4 | 17.45 |
|  | 45 | 0.63 | 10.83 | 0.60 | 10.83 | 1.13 | 6.64 | 0.33 | 16.74 |
|  | 30 | 0.50 | 3.90 | 0.46 | 3.90 | 0.8 | 8.53 | 0.26 | 13.41 |
| 10 | 60 | 0.27 | 8.10 | 0.23 | 8.10 | 0.46 | 9.03 | 0.26 | 26.81 |
|  | 45 | 0.20 | 9.97 | 0.13 | 9.97 | 0.33 | 10.57 | 0.20 | 22.42 |
|  | 30 | 0.13 | 15.22 | 0.1 | 15.22 | — | — | 0.16 | 22.53 |

The data presented in Table 24 suggests that strength gain is exponentially dependent on set time. The gained strength is also dependent on the test temperature, where in lowering the test temperatures effect the set time minimally compared to the higher temperatures.

The test results presented in Tables 23 and 24 are summarized in FIG. 11 through FIG. 14. The test results indicate that the strength of the tack coat type is nonlinearly dependent on the set time and test temperatures. Although the strength depends on other factors such as wind velocity, pavement temperature, relative humidity, a relationship between the only two of the factors was developed because these two parameters were the only ones evaluated.

To develop a relationship between gained strength and set time and test temperature, various combinations were evaluated and the following relationship provided the best $R^2$ values:

$$\text{Strength} = \text{Set Time} * \text{Time Factor} * e^{(Test\ Temperature * Temperature\ Factor)} \quad \text{Eq. (1)}$$

where set time is in minutes and test temperature is in ° F. The time and temperature factors for each tack coat type along with $R^2$ values is presented in Table 25. Since DS tests were not performed at all temperatures, separate relationships were developed for the two devices. The $R^2$ values are higher than 0.84 indicating that a good correlation exists and these relationships could be used for the evaluation of tack coat in the field.

TABLE 25

| Tack Coat | POD Time Factor | POD Temp Factor | POD $R^2$ | Direct Shear Time Factor | Direct Shear Temp Factor | Direct Shear $R^2$ |
|---|---|---|---|---|---|---|
| CSS-1h | 0.001171 | 0.02668 | 1.00 | 0.00087346 | 0.04032966 | 0.99 |
| CSS-1 | 0.000930 | 0.027128 | 0.99 | 0.00092019 | 0.03498492 | 0.98 |
| SS-1h | 0.001242 | 0.022992 | 0.96 | 0.00434779 | 0.01249838 | 0.84 |
| PG64-22 | 0.003392 | 0.018231 | 0.95 | 0.00356082 | 0.02171078 | 0.89 | b. Verification Tests Performed in the Field Parking Lot

To validate the relationships proposed in Eq. 1 and Table 25, a few tests were performed in a parking lot using the POD. The tests were performed at two set times 20 and 30 minutes and at two different times: 7:00 AM and 4:00 PM. The tests were performed at one application rate of 0.18 $1/m^2$ and 18 kg load was maintained for 10 minutes before performing tests. The tests were performed in triplicate and for three tack coat types: CSS-1h, CSS-1, and PG64-22. The data is presented in Tables 26 through 28. The results presented show the field test conditions including test temperature and set time. In addition, tables show measured strength in the parking lot using POD and estimated strength based on relationships presented in Table 25.

The CSS-1h emulsion evaluation results are summarized in Table 26. The test results indicate that the DS estimated strength closely matches with measured POD strength. For example, POD measured strength is 1.12 kPa while estimated strength is 0.91 and 1.26 kPa for POD and DS devices, respectively. The results show that POD estimated strength is closer to the measured values at lower temperature but are different at higher temperatures for 30 minutes set time.

The CSS-1 emulsion test results are summarized in Table 27. The test results indicate that the POD estimated and measured strength closely matches. For example, the measured strength is 1.26 kPa for a set time of 30 minutes and at test temperature of 21° C. while estimated strength is 1.33 kPa. Similarly, the estimated strength (1.05 kPa) is different from the measured strength (1.75 kPa) at test temperature of 25° C. and 20 minutes set time. The test results also indicate that the DS estimated strength is higher than the measured POD strength.

The PG64-22 test results are summarized in Table 27. The test results show similar trends to that of CSS-1 emulsion. The test results show that the estimated and measured POD values are very similar while DS over estimated the strength.

The difference between estimated and measured strength could be due to environmental factors such as pavement temperature, wind velocity, relative humidity, etc. The results suggest that these factors should be monitored as well to see if these parameters can reduce the differences between the measured and estimated strength.

In general, test results indicate that POD and DS estimated strengths are similar to the parking lot test results. In addition, DS device over estimated strength in comparison to POD device. The results also indicate that the proposed system can be used in the evaluation of tack coat quality in the field.

TABLE 26

| Residual App. Rate $1/m^2$ | Load, kg | Test Temp. ° C. | Set Temp, min | Average Strengths, psi Measured POD | Average Strengths, psi Estimated POD | Average Strengths, psi Estimated DS |
|---|---|---|---|---|---|---|
| 0.18 | 18 | 9 | 20 | .12 | .09 | .12 |
|  |  |  | 30 | .16 | .13 | .8 |
|  |  | 18 | 20 | .22 | .13 | .23 |
|  |  |  | 30 | .31 | .19 | .35 |

TABLE 27

| Residual | | | | Average Strengths, psi | | |
|---|---|---|---|---|---|---|
| App. Rate | Load, | Test Temp. | Set Time, | Measured | Estimated | |
| l/m² | kg | ° C. | min | POD | POD | DS |
| 0.18 | 18 | 21 | 20 | .12 | .12 | .21 |
| | | | 30 | .18 | .19 | .32 |
| | | 25 | 20 | .25 | .15 | .27 |
| | | | 30 | .29 | .23 | .41 |

TABLE 28

| Residual | | | | Average Strengths, kPa | | |
|---|---|---|---|---|---|---|
| APP. Rate | Load, | Test Temp. | Set Time, | Measured | Estimated | |
| l/m² | kg | ° C. | min | POD | POD | DS |
| 0.18 | 18 | 21 | 20 | .12 | .18 | .22 |
| | | | 30 | .18 | .26 | .33 |
| | | 25 | 20 | .18 | .21 | .27 |
| | | | 30 | .26 | .31 | .40 |

The POD was also evaluated at a test site. On the site, CSS-1h emulsion type was used with 90% dilution with water and the residual application rate was 0.25 gal/yd². The results of the evaluation are shown in Table 29. The tests results indicate that the measured strength is similar to the estimated strength. For example, the measured shear strength at 30 minutes of set time was 0.2 psi while estimated strength was 0.18 psi. Overall for all of the set times, the measured strength was slightly higher than the estimated strength indicating that the tack coat quality is adequate.

TABLE 29

| Dilution Level | Residual Application Rate Gal/yd² | Load, kg | Set Time, min | Measured Strength, psi | Estimated Strength, psi |
|---|---|---|---|---|---|
| 90/10 | 0.25 | 18 | 20 | .13 | .12 |
| | Ambient | | 30 | .20 | .18 |
| | Temperature, | | 40 | .27 | .25 |
| | 17° C. | | 50 | .33 | .31 |
| | | | 60 | .37 | .37 |

The example showed that the POD and the proposed method of estimating strength based on set time and test temperature can identify the quality of an applied tack coat. Further, the POD device, having similar results to the direct shear device is more versatile since the pull off mode of testing is independent of the surface tested. Therefore, the POD can be used in the field to identify the quality of a tack coat. In addition, because of the setup time and convenience of the POD, the quality of the tack coat can be done in less than 45 minutes after the tack coat has been applied.

Example 4

A Statistical Analysis

The ability of an apparatus with support members and an apparatus without support members was evaluated using an analysis of variance (ANOVA) test performed using MINITAB® 14.11. The test identified if the devices can successfully determine the impact of changes in a test parameter. The measured strength in the field was considered to be a dependent factor while set time, applied load, application rate and test temperature were considered to be independent parameters.

The null hypothesis selected for the ANOVA was that the means measured with the devices are the same. In other words, the measured strength does not depend on the independent parameter. If the null hypothesis is rejected, it can be concluded that the strength is dependent on the independent parameters. Thus, the devices are able to identify the impact of dependent parameters. A confidence level of 95% was assumed for the analysis purpose. The probability factor of falsely rejecting the null hypothesis (p-value) should be less than 0.05 in order to conclude that a difference is significant, since a 95% confidence level was chosen. The null hypothesis was rejected when the p-value was less than 0.05 and was accepted when the p-value was greater than 0.05.

The results of the ANOVA analysis for an apparatus with support members, POD and an apparatus without any support members (simple pull off device, SPOD), was conducted for six different tack coat types, such as CSS-1h for the POD and SPOD shown in Tables 30 and 31, respectively. Since the objective of the statistical analyses was to compare the two devices, the tables for POD and SPOD for each tack coat types are placed one after the other. In each table, rows 2 through 5 show the results of the main effects while rows 6 through 17 show the effects of interactions. The first column shows evaluated factors and their interactions. The second column shows degree of freedom and the third column shows sum of squares. The fourth column shows F-statistics and the fifth column shows p-value obtained. The sixth column shows the conclusion of the ANOVA analysis. The Y in the sixth column indicates that the device is able to identify the effect of parameter changes while N in the sixth column indicates that the effect of the parameter is insignificant.

The CSS-1h emulsion evaluation results of are summarized in Table 30. The evaluation results indicate that four-way interaction effects are present. However, the three-way interaction effects are not significant expect for interaction effect of application rate, for test temperature and applied load where the interaction effect is significant. In terms of two-way interaction, the effect is significant in four cases and insignificant in two cases (for set time and application rate and set time and test temperature). The results summarized in Table 30 also indicate that the main effect is significant. In other words, the device is able to identify the effect of changes in independent parameter. Overall ANOVA of the POD data suggests that the device is able to discriminate between parameters because means are not similar.

TABLE 30

| Source | Degree of Freedom | SS | F Stat | PValue | Statistically Significant (Y/N) |
|---|---|---|---|---|---|
| Set | 1 | 0.59405 | 84.15 | <0.001 | Y |
| Rate | 1 | 2.8322 | 401.18 | <0.001 | Y |
| Temp | 1 | 4.46009 | 631.77 | <0.001 | Y |
| Load | 2 | 1.63184 | 115.57 | <0.001 | Y |
| Set * Rate | 1 | 0.0128 | 1.81 | 0.184 | N |
| Set * Temp | 1 | 0.01742 | 2.47 | 0.123 | N |
| Set * Load | 2 | 0.05492 | 3.89 | 0.027 | Y |
| Rate * Temp | 1 | 0.10734 | 15.2 | <0.001 | Y |
| Rate * Load | 2 | 0.36461 | 25.82 | <0.001 | Y |
| Temp * Load | 2 | 0.19089 | 13.52 | <0.001 | Y |
| Set * Rate * Temp | 1 | 0.01681 | 2.38 | 0.129 | N |

TABLE 30-continued

| Source | Degree of Freedom | SS | F Stat | PValue | Statistically Significant (Y/N) |
|---|---|---|---|---|---|
| Set * Temp * Load | 2 | 0.01239 | 0.88 | 0.422 | N |
| Rate * Temp * Load | 2 | 0.06367 | 4.51 | 0.016 | Y |
| Set * Rate * Load | 2 | 0.02861 | 2.03 | 0.143 | N |
| Set * Rate * Temp * Load | 2 | 0.06367 | 4.28 | 0.020 | Y |
| Error | 48 | 0.33887 | | | |
| Total | 71 | | | | |

The CSS-1h emulsion evaluation results of SPOD are summarized in Table 31. The evaluation results indicate that there is no four-way interaction present. In addition, the three-way interaction is significant expect for application rate, test temperature and applied load where the interaction effect is insignificant. In terms of two-way interaction, the interaction effect is significant in two cases and insignificant in three cases (for set time and application rate, for set time and applied load, and for application rate and applied load). The results summarized in Table 31 indicate that the main effect is significant. In other words, the device is able to identify the effect of changes in independent parameter. Overall ANOVA of the SPOD data suggests that the device is able to discriminate between the parameters because means are not similar.

TABLE 31

| Source | Degree of Freedom | SS | F Stat | PValue | Statistically Significant (Y/N) |
|---|---|---|---|---|---|
| Set | 1 | 0.22781 | 23.51 | <0.001 | Y |
| Rate | 1 | 0.86023 | 88.77 | <0.001 | Y |
| Temp | 1 | 2.40901 | 248.6 | <0.001 | Y |
| Load | 2 | 1.71661 | 88.57 | <0.001 | Y |
| Set * Rate | 1 | 0.0165 | 1.7 | 0.198 | N |
| Set * Temp | 1 | 0.09031 | 9.32 | 0.004 | Y |
| Set * Load | 2 | 0.01886 | 0.97 | 0.385 | N |
| Rate * Temp | 1 | 0.71401 | 73.68 | <0.001 | Y |
| Rate * Load | 2 | 0.04972 | 2.57 | 0.870 | N |
| Temp * Load | 2 | 0.20881 | 10.77 | <0.001 | Y |
| Set * Rate * Temp | 1 | 0.0042 | 0.43 | 0.513 | N |
| Set * Temp * Load | 2 | 0.01323 | 0.68 | 0.510 | N |
| Rate * Temp * Load | 2 | 0.10681 | 5.51 | 0.007 | Y |
| Set * Rate * Load | 2 | 0.00994 | 0.51 | 0.602 | N |
| Set * Rate * Temp * Load | 2 | 0.0247 | 1.27 | 0.289 | N |
| Error | 48 | 0.46513 | | | |
| Total | 71 | | | | |

Similar patterns were observed with remaining tack coat types (e.g., CSS-1, SS-1h, SS-1, RC-250, and PG64-22). Typically results indicated that both devices can identify the main effects while significance and insignificance of interactions effects changed with changes in emulsion types with an exception of RC-250.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. For example, it will be apparent that certain compositions which are chemically related may be substituted for the compositions described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Caduto, D. P. (1999), *Geotechnical Engineering Principles and Practicies*, Prentice Hall, NJ.

Hachiya, Y. and Sato, K. "Effect of Tack Coat on Bonding Characteristics at Interface Between Asphalt Concrete Layers," *Eight International Conference on Asphalt Pavements Proceedings*, Volume 1, pp. 349–362, 1997.

Mohammad, L. N., Raqib, Md. A., and Huang, B. "Influence of Asphalt Tack Coat Materials on the Interface Shear Strength," Presented at $81^{st}$ Transportation Research Board Annual Meeting, January 13–17, Washington, D.C., 2002.

Romanoschi, S. A. and Metcalf, J. B. "Characterization of Asphalt Concrete Layer Interfaces," *Transportation Research Record* 1778, Transportation Research Board, Washington, D.C., 2001.

Santagata, E., Canestrari, F., and Santagata, F. A. (1993), "Laboratory Shear Testing of Tack Coat Emulsions," $1^{st}$ *World Congress on Emulsion*, Paris, 1993.

Tandon, V., Deysarkar, I. and Meshkani, A. (2004), "Evaluation of UPOD and SPOD devices to identify the Quality of Tack Coat," Submitted for Publication in the Journal of Transportation Research Board and Presentation in 84th Annual Meeting of Transportation Research Board, Washington, D.C., 2005

Uzan, J., M. Livneh, and Y. Eshed, "Investigation of Adhesion Properties Between Asphaltic-Concrete Layers," Journal of Asphalt Paving Technologists, Volume 47, p. 495, 1978

Youtcheff, J and Aurilio, V. "Moisture Sensitivity of Asphalt Binders: Evaluation and Modeling of the Pneumatic Adhesion Test Results," *Proceedings of the Annual Conference—Canadian Technical Asphalt Association* 0068-984X, Issue 42, pp. 180–200, 1997.

The invention claimed is:

1. An apparatus, comprising:
a plurality of supporting members, each being adjustable to a plurality of heights;
a contact plate coupled to the plurality of supporting members, the contact plate comprising a flexible layer for conforming and adhering to a pavement surface; and
a torque wrench and a force measuring device coupled to the supporting members, the torque wrench and the force measuring device pulling up the contact plate to determine the adhesive quality of a tack coat applied to the pavement surface.

2. The apparatus of claim 1, the flexible layer comprising an adhesive layer and adhesive agents.

3. The apparatus of claim 1, the flexible layer comprising a moisture-bearing foam.

4. The apparatus of claim 1, further comprising a load placed on the contact plate to conform the contact plate to the surface for stability.

5. The apparatus of claim 4, the load comprising approximately 20 to 75 pounds.

6. The apparatus of claim 1, the supporting members being operably moveable in a horizontal plane between the range of approximately 0° to 20°.

7. The apparatus of claim 1, further comprising an elevation member coupled to the plate, the elevation member operably moveable to place the plate in contact with the surface.

8. The apparatus of claim 7, the elevation member comprising a cylinder.

9. The apparatus of claim 8, the cylinder comprising a hydraulic-controlled cylinder.

10. The apparatus of claim 8, the cylinder comprising a spring-loaded cylinder.

11. The apparatus of claim 8, the cylinder comprising a motor-controlled cylinder.

12. The apparatus of claim 9, the cylinder comprising a pneumatic-controlled cylinder.

13. The apparatus of claim 12, the pneumatic-controlled cylinder further comprising a sensor for measuring air-pressure or vacuum-pressure.

14. The apparatus of claim 1, the plurality of supporting members comprising three supporting members positioned in a tripod configuration.

15. he apparatus of claim 1, the pavement surface comprising a tack coat layer.

16. An apparatus comprising:
supporting members being adjustable to a plurality of heights;
a contact pate comprising a flexible layer for conforming and adhering to a pavement surface;
an elevation member coupled to the supporting members and the contact plate, the elevation member moving the contact plate coupled to the elevation member in direct contact with the pavement surface; and
a torque wrench and a force measuring device coupled to the supporting members for testing the adhesive quality of a tack coat applied to the pavement surface.

17. The apparatus of claim 16, the contact plate being substantially parallel to the pavement surface.

18. The apparatus of claim 16, the flexible layer comprising an adhesive layer.

19. The apparatus of claim 16, the flexible layer comprising a moisture-bearing foam.

20. The apparatus of claim 16, the supporting members being operably moveable in a horizontal plane.

21. A method, comprising:
adjusting a plurality of supporting members to a height;
placing a contact plate coupled to the plurality of support members in direct contact with a pavement surface, where the contact plate comprises a flexible layer for adhering and conforming to the pavement surface;
applying a load to contact plate to adhere the contact plate to the pavement surface;
rotating a torque wrench about an axis to pull off the contact plate for determining the adhesive quality of a tack coat applied to the pavement surface.

22. The method of claim 21, the step of adjusting the support members comprising adjusting the height of at least one of the plurality of support members.

23. The method of claim 21, the step of adjusting the support members comprising moving the support members in a horizontal plane.

24. The method of claim 21, further comprising adjusting an elevation member to place the contact plate in direct contact with the surface.

25. The method of claim 24, the step of adjusting comprising moving the elevation member in a vertical manner.

26. The method of claim 21, the load comprising approximately 20 to 75 pounds.

27. The method of claim 21, further comprising measuring the force of pulling up a contact plate with a force measuring device.

* * * * *

UNITED STATES PATENT AND TRADEMARK OFFICE
CERTIFICATE OF CORRECTION

PATENT NO.       : 7,162,929 B2
APPLICATION NO.  : 10/937102
DATED            : January 16, 2007
INVENTOR(S)      : Vivek Tandon It is certified that error appears in the above-identified patent and that said Letters Patent is hereby corrected as shown below:

Column 21, line 29, please delete "he" and insert --The--.

Column 21, line 34, please delete "pate" and insert --plate--.

Column 22, line 19, after "surface;" please add --and--.

Signed and Sealed this

Nineteenth Day of June, 2007

JON W. DUDAS
*Director of the United States Patent and Trademark Office*